US005976541A

United States Patent [19]

Berzofsky et al.

[11] Patent Number: 5,976,541

[45] Date of Patent: Nov. 2, 1999

[54] POTENT PEPTIDE FOR STIMULATION OF CYTOTOXIC T LYMPHOCYTES SPECIFIC FOR THE HIV-1 ENVELOPE

[75] Inventors: Jay A. Berzofsky, Bethesda; Toshiyuki Taskeshita; Mutsunori Shirai, both of Rockville; C. David Pendleton, Bethesda, all of Md.; Steven Kozlowski, Washington, D.C.; David H. Margulies, Bethesda, Md.

[73] Assignee: The United States of America as represented by the Department of Health and Human Services, Washington, D.C.

[21] Appl. No.: 07/847,311

[22] Filed: Mar. 6, 1992

Related U.S. Application Data

[63] Continuation-in-part of application No. 07/760,530, Sep. 18, 1991, Pat. No. 5,820,865, which is a continuation-in-part of application No. 07/148,592, Jan. 26, 1988, abandoned.

[51] Int. Cl.[6] .......................... A61K 39/21; A61K 39/38; A61K 39/12; C12N 15/00

[52] U.S. Cl. .................................... 424/188.1; 424/184.1; 424/204.1; 424/208.1; 435/172.3; 435/235.1; 530/326

[58] Field of Search ............................. 435/172.3, 235.1; 530/326; 424/89, 184.1, 188.1, 204.1, 208.1

[56] References Cited

U.S. PATENT DOCUMENTS

| | | | |
|---|---|---|---|
| 5,013,548 | 5/1991 | Haynes et al. . | |
| 5,019,387 | 5/1991 | Haynes et al. | 424/89 |
| 5,562,905 | 10/1996 | Kenealy et al. | 424/188.1 |

FOREIGN PATENT DOCUMENTS

| | | |
|---|---|---|
| 0273716 | 7/1988 | European Pat. Off. . |
| 0 402 088 A3 | 12/1990 | European Pat. Off. . |
| 0 490 667 A3 | 6/1992 | European Pat. Off. . |
| 0 518 672 A2 | 12/1992 | European Pat. Off. . |
| WO86/02383 | 4/1986 | WIPO . |
| 8702775 | 5/1987 | WIPO . |
| WO87/02775 | 5/1987 | WIPO . |
| WO87/07616 | 12/1987 | WIPO . |
| 89/07112 | 8/1989 | WIPO . |
| 91/02544 | 3/1991 | WIPO . |
| 91/14449 | 10/1991 | WIPO . |
| 93/05812 | 4/1993 | WIPO . |

OTHER PUBLICATIONS

"Serum angiotensin–1 converting enzyme . . . by major Histocompability Complex Class I molecules", S. Kozlowski et al, Journal of Experimental Medicine, vol. 175, No. 6, Jun. '92, pp. 1417–1422.

"A unique subunit immunogen . . . CD8–positive CTLs", H. Takahashi et al, Vaccines 91, 1991, Cold Spring harbor Laboratory, pp. 1–7.

"Induction of cytotoxic T cells to HIV proteins", J. Berzofsky et al, Aids Research and Human Retroviruses, vol. 7, No. 2, Feb. 1991, p. 144.

"An immunodominant class I–restricted . . . class II–restricted help for itself", H. Takahashi et al., Journal of Experimental Medicine, vol. 171, No. 2, Feb. 1990, pp. 571–576.

"A component of fetal calf . . . into its active form", S. Kozlowski et al, Journal of Cellular Biochemistry, No. 16D, Mar. 1992, p. 66.

Berzofsky et al., "Method to Induce Cytotoxic T Lymphocytes Specific for a Broad Array of HIV–1 Isolates Using Hybrid Synthetic Peptides", Gov't of the USA, Dept. of Health and Human Services, Sep. 18, 1991.

Takahashi et al, The Journal of Exp. Med., vol. 170, pp. 2023–2035 (1989).

Fundamental Immunology, Second Edition, Edited by Williams E. Paul, M.D., Raven Press Ltd., New York (1989).

Benjamin et al, Ann. Rev. Immunol., 2:67–101 (1984).

Kast et al, J. Exp. Med., 164:723–738 (1986).

Chakrabarti et al, Nature, 320:535–537 (1986).

Bennink et al, Nature, 311:578–579 (1984).

Houghten, Proc. Natl. Acad. Sci. USA, 82:5131–5135 (1985).

Takahashi, H. et al., *Science*, 246:118–121, 1989.

Cease, et al., Proc. Natl. Acad. Sci., U.S.A., 84; 4249–4253, Jun. 1987.

Ratner, et al., Nature, 313; 277–284, Jan. 1985.

De Lisi, et al., Proc. Natl. Acad. Sci., U.S.A., 82; 7048–7052, Oct. 1985.

Happ, et al., Proc. Natl. Acad. Sci., USA, 78(6); 3824–3828, Jun. 1981.

Hopp, J. of Immunological Methods; 88; 1–18; 1986.

Chau, et al., Biochem., 13(2); 211–221, Jan. 1974.

Chou, et al., Ann. Rev. Biochem., 47; 251–76; 1978.

Kozlowsky et al, Keystone Symposium on Antigen Presentation: Function of the MHC. TAOS NM Mar. 5–11, 1992. 66. Abstract.

Takahashi et al, "In Immunodominant epitopes of the (HIV)(env) Glyoprotein gp160 recognized by Class I(MHC) Molecule–restordel Murine (CTL)." PNAS. 85, pp. 3105–3108, May 1988.

Fultz, PN et al "Infection of Non–Human Primates with Human and Simian Immunodefiency Viruses" AIDS Vaccine Research and Clincial Trials. Putney SD et al Editors NY 1990 p. 339–49 abstract.

Hilleman, M.R. "Conclusions: In Pursut of an AIDS Viruses Vaccine" Abstract, Immunol Ser. 44:605–20, 1989.

Echberg, J.W. "Experience with 13 HIV Efficieny trials in Chimpanzees" Int Confon AIDS Jun. 20–23, 1990, 6(1) p. 204, Abstract Th.A.338.

Fauci, A.S. et al "Development and Evaluation of a Vaccine for HIV Infection" Ann. Int Med. May 1, 1989, 110(5) pp. 373–385.

*Primary Examiner*—Lynette F. Smith
*Assistant Examiner*—Brett Nelson
*Attorney, Agent, or Firm*—Townsend and Townsend and Crew LLP

[57] ABSTRACT

Peptides having high activity in the eliciting of a cytotoxic T lymphocyte response to the HIV-1 envelope glycoprotein gpl60 are described. The activation of 12–15 residue peptides by proteolytic degradation to shorter peptides is shown as are general techniques for characterizing such activation processes.

5 Claims, 9 Drawing Sheets

| | 315 | | | | | | | | | | | | | | 329 |
|---|---|---|---|---|---|---|---|---|---|---|---|---|---|---|---|
| 18IIIB (P18) | R | I | Q | R | G | P | G | R | A | F | V | T | I | G | K |
| 18RF | △ | △ | T | K | G | P | G | R | V | I | Y | A | T | G | Q |
| 18-1 | △ | | | | | | | | | | | | | | |
| 18-2 | | △ | | | | | | | | | | | | | |
| 18-3 | | | T | | | | | | | | | | | | |
| 18-4 | | | | K | | | | | | | | | | | |
| 18-5 | | | | | A | | | | | | | | | | |
| 18-6 | | | | | | A | | | | | | | | | |
| 18-7 | | | | | | | A | | | | | | | | |
| 18-8 | | | | | | | | A | | | | | | | |
| 18-9 | | | | | | | | | V | | | | | | |
| 18-10 | | | | | | | | | | I | | | | | |
| 18-11 | | | | | | | | | | | Y | | | | |
| 18-12 | | | | | | | | | | | | A | | | |
| 18-13 | | | | | | | | | | | | | T | | |
| 18-14 | | | | | | | | | | | | | | A | |
| 18-15 | | | | | | | | | | | | | | | Q |
| 18I10 | | | | R | G | P | G | R | A | F | V | T | I | | |

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
(A) LENGTH: 15 amino acids
(B) TYPE: amino acid
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Human Immunodeficiency Virus Type I
(B) STRAIN: IIIB (ix) FEATURE:
(A) NAME/KEY: Peptide
(B) LOCATION: 1..15
(D) OTHER INFORMATION: /label= peptide
/note= "Cytotoxic T lymphocyte immunodominant peptide of HIV-I envelope glycoprotein from strain IIIB; activatible by protease cleavage to core (ix) FEATURE:
(A) NAME/KEY: Peptide
(B) LOCATION: 4..13
(D) OTHER INFORMATION: /label= peptide
/note= "Highly immunogenic core peptide from immunodominant region of envelope glycoprotein of HIV-I strain IIIb; peptide p18-I-10"

(ix) FEATURE:
(A) NAME/KEY: Peptide
(B) LOCATION: 5..13
(D) OTHER INFORMATION: /label= peptide
/note= "peptide p18-I-9"

(ix) FEATURE:
(A) NAME/KEY: Peptide
(B) LOCATION: 4..12
(D) OTHER INFORMATION: /label= peptide
/note= "peptide p18-T-9"

(ix) FEATURE:
(A) NAME/KEY: Peptide
(B) LOCATION: 3..11
(D) OTHER INFORMATION: /label= peptide
/note= "peptide p18-V-9"

(ix) FEATURE:
(A) NAME/KEY: Peptide
(B) LOCATION: 2..11
(D) OTHER INFORMATION: /label= peptide
/note= "peptide p18-V-10"

(xi) SEQUENCE DESCRIPTION: SEQ ID NO:1:

```
Arg Ile Gln Arg Gly Pro Gly Arg Ala Phe Val Thr Ile Gly Lys
1               5                   10                  15
```

(2) INFORMATION FOR SEQ ID NO:2:

(i) SEQUENCE CHARACTERISTICS:
(A) LENGTH: 15 amino acids
(B) TYPE: amino acid
(D) TOPOLOGY: linear (ii) MOLECULE TYPE: peptide -continued (iii) HYPOTHETICAL: NO (v) FRAGMENT TYPE: internal (vi) ORIGINAL SOURCE:
(A) ORGANISM: Human Immunodeficiency Virus Type I
(B) STRAIN: MN (ix) FEATURE:
(A) NAME/KEY: Peptide
(B) LOCATION: 1..15
(D) OTHER INFORMATION: /label= peptide
/note= "Cytotoxic T lymphocyte immunodominant peptide from envelope glycoprotein from HIV-1 strain MN; activatible by protease digestion to (ix) FEATURE:
(A) NAME/KEY: Peptide
(B) LOCATION: 4..13
(D) OTHER INFORMATION: /label= peptide
/note= "Highly immunogenic core peptide from immunodominant region of envelope glycoprotein of HIV-I strain MN; peptide p18MN-T-10."

(xi) SEQUENCE DESCRIPTION: SEQ ID NO:2:

```
Arg Ile His Ile Gly Pro Gly Arg Ala Phe Tyr Thr Thr Lys Asn
1               5                   10                  15
```

(2) INFORMATION FOR SEQ ID NO:3:

(i) SEQUENCE CHARACTERISTICS:
(A) LENGTH: 15 amino acids
(B) TYPE: amino acid
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Human Immunodeficiency Virus Type I
(B) STRAIN: RF (ix) FEATURE:
(A) NAME/KEY: Peptide
(B) LOCATION: 1..15
(D) OTHER INFORMATION: /label= peptide
/note= "Cytotoxic T lymphocyte immunodominant peptide from envelope glycoprotein of HIV-1 strain RF; activatible to core peptide by protease (ix) FEATURE:
(A) NAME/KEY: Peptide
(B) LOCATION: 4..13
(D) OTHER INFORMATION: /label= peptide
/note= "Highly immunogenic core peptide of immunodominant region of envelope glycoprotein of HIV-I strain RF."

(ix) FEATURE:
(A) NAME/KEY: Peptide
(B) LOCATION: 3..15
(D) OTHER INFORMATION: /label= peptide
/note= "peptide 18RF 315-329(delta-delta)"

(xi) SEQUENCE DESCRIPTION: SEQ ID NO:3:

```
Ser Ile Thr Lys Gly Pro Gly Arg Val Ile Tyr Ala Thr Gly Gln
1               5                   10                  15
```

(2) INFORMATION FOR SEQ ID NO:4:

(i) SEQUENCE CHARACTERISTICS:
(A) LENGTH: 15 amino acids
(B) TYPE: amino acid

-continued (D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Human Immunodeficiency Virus Type I
(B) STRAIN: SC (ix) FEATURE:
(A) NAME/KEY: Peptide
(B) LOCATION: 1..15
(D) OTHER INFORMATION: /label= peptide
/note= "Cytotoxic T lymphocyte immunodominant peptide from envelope glycoprotein from HIV-1 strain SC; activatible by protease digestion to (ix) FEATURE:
(A) NAME/KEY: Peptide
(B) LOCATION: 4..13
(D) OTHER INFORMATION: /label= peptide
/note= "Highly immunogenic core peptide of immunodominant region of envelope glycoprotein from HIV-I strain SC."

(xi) SEQUENCE DESCRIPTION: SEQ ID NO:4:

```
Ser Ile His Ile Gly Pro Gly Arg Ala Phe Tyr Ala Thr Gly Asp
1               5                   10                  15
```

(2) INFORMATION FOR SEQ ID NO:5:

(i) SEQUENCE CHARACTERISTICS:
(A) LENGTH: 15 amino acids
(B) TYPE: amino acid
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Human Immunodeficiency Virus Type I
(B) STRAIN: WMJ-2

(ix) FEATURE:
(A) NAME/KEY: Peptide
(B) LOCATION: 1..15
(D) OTHER INFORMATION: /label= peptide
/note= "Cytotoxic T lymphocyte immunodominant peptide from envelope glycoprotein from HIV-1 strain WMJ-2; activatible by protease digestion to (ix) FEATURE:
(A) NAME/KEY: Peptide
(B) LOCATION: 4..13
(D) OTHER INFORMATION: /label= peptide
/note= "Highly immunogenic core peptide of immunodominant region of envelope glycoprotein from HIV-I strain WMJ-2."

(xi) SEQUENCE DESCRIPTION: SEQ ID NO:5:

```
Ser Leu Ser Ile Gly Pro Gly Arg Ala Phe Arg Thr Arg Glu Ile
1               5                   10                  15
```

(2) INFORMATION FOR SEQ ID NO:6:

(i) SEQUENCE CHARACTERISTICS:
(A) LENGTH: 15 amino acids
(B) TYPE: amino acid
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Human Immunodeficiency Virus Type I
(B) STRAIN: Z321

(ix) FEATURE:
(A) NAME/KEY: Peptide
(B) LOCATION: 1..15
(D) OTHER INFORMATION: /label= peptide
/note= "Cytotoxic T lymphocyte immunodominant peptide from envelope glycoprotein from HIV-1 strain Z321; activatible by protease digestion to (ix) FEATURE:
(A) NAME/KEY: Peptide
(B) LOCATION: 4..13
(D) OTHER INFORMATION: /label= peptide
/note= "Highly immunogenic core peptide of immunodominant region of envelope glycoprotein from HIV-I strain Z321."

(xi) SEQUENCE DESCRIPTION: SEQ ID NO:6:

```
Ser Ile Ser Ile Gly Pro Gly Arg Ala Phe Phe Ala Thr Thr Asp
1               5                   10                  15
```

(2) INFORMATION FOR SEQ ID NO:7:

(i) SEQUENCE CHARACTERISTICS:
(A) LENGTH: 15 amino acids
(B) TYPE: amino acid
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Human Immunodeficiency Virus Type I
(B) STRAIN: SF2

(ix) FEATURE:
(A) NAME/KEY: Peptide
(B) LOCATION: 1..15
(D) OTHER INFORMATION: /label= peptide
/note= "Cytotoxic T lymphocyte immunodominant peptide from envelope glycoprotein from HIV-1 strain SF2; activatible by protease digestion to (ix) FEATURE:
(A) NAME/KEY: Peptide
(B) LOCATION: 4..13
(D) OTHER INFORMATION: /label= peptide
/note= "Highly immunogenic core peptide of immunodominant region of envelope glycoprotein from HIV-I strain SF2."

(xi) SEQUENCE DESCRIPTION: SEQ ID NO:7:

```
Ser Ile Tyr Ile Gly Pro Gly Arg Ala Phe His Thr Thr Gly Arg
1               5                   10                  15
```

(2) INFORMATION FOR SEQ ID NO:8:

(i) SEQUENCE CHARACTERISTICS:
(A) LENGTH: 15 amino acids
(B) TYPE: amino acid
(D) TOPOLOGY: linear (ii) MOLECULE TYPE: peptide -continued (iii) HYPOTHETICAL: NO (v) FRAGMENT TYPE: internal (vi) ORIGINAL SOURCE:
(A) ORGANISM: Human Immunodeficiency Virus Type I
(B) STRAIN: NY5

(ix) FEATURE:
(A) NAME/KEY: Peptide
(B) LOCATION: 1..15
(D) OTHER INFORMATION: /label= peptide
/note= "Cytotoxic T lymphocyte immunodominant peptide from envelope glycoprotein from HIV-1 strain NY5; activatible by protease digestion to (ix) FEATURE:
(A) NAME/KEY: Peptide
(B) LOCATION: 4..13
(D) OTHER INFORMATION: /label= peptide
/note= "Highly immunogenic core peptide of immunodominant region of envelope glycoprotein from HIV-I strain NY5."

(xi) SEQUENCE DESCRIPTION: SEQ ID NO:8:

```
Gly Ile Ala Ile Gly Pro Gly Arg Thr Leu Tyr Ala Arg Glu Lys
1               5                   10                  15
```

(2) INFORMATION FOR SEQ ID NO:9:

(i) SEQUENCE CHARACTERISTICS:
(A) LENGTH: 15 amino acids
(B) TYPE: amino acid
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Human Immunodeficiency Virus Type I
(B) STRAIN: CDC4

(ix) FEATURE:
(A) NAME/KEY: Peptide
(B) LOCATION: 1..15
(D) OTHER INFORMATION: /label= peptide
/note= "Cytotoxic T lymphocyte immunodominant peptide from envelope glycoprotein from HIV-1 strain CDC4; activatible by protease digestion to (ix) FEATURE:
(A) NAME/KEY: Peptide
(B) LOCATION: 4..13
(D) OTHER INFORMATION: /label= peptide
/note= "Highly immunogenic core peptide of immunodominant region of envelope glycoprotein from HIV-I strain CDC4."

(xi) SEQUENCE DESCRIPTION: SEQ ID NO:9:

```
Arg Val Thr Leu Gly Pro Gly Arg Val Trp Tyr Thr Thr Gly Glu
1               5                   10                  15
```

(2) INFORMATION FOR SEQ ID NO:10:

(i) SEQUENCE CHARACTERISTICS:
(A) LENGTH: 15 amino acids
(B) TYPE: amino acid
(D) TOPOLOGY: linear (ii) MOLECULE TYPE: peptide (iii) HYPOTHETICAL: NO -continued (v) FRAGMENT TYPE: internal (vi) ORIGINAL SOURCE:
(A) ORGANISM: Human Immunodeficiency Virus Type I
(B) STRAIN: Z3

(ix) FEATURE:
(A) NAME/KEY: Peptide
(B) LOCATION: 1..15
(D) OTHER INFORMATION: /label= peptide
/note= "Cytotoxic T lymphocyte immunodominant peptide from envelope glycoprotein from HIV-1 strain Z3; activatible by protease digestion to (ix) FEATURE:
(A) NAME/KEY: Peptide
(B) LOCATION: 4..13
(D) OTHER INFORMATION: /label= peptide
/note= "Highly immunogenic core peptide of immunodominant region of envelope glycoprotein from HIV-I strain Z3."

(xi) SEQUENCE DESCRIPTION: SEQ ID NO:10:

Ser Ile Arg Ile Gly Pro Gly Lys Val Phe Thr Ala Lys Gly Gly
1 5 10 15

(2) INFORMATION FOR SEQ ID NO:11:

(i) SEQUENCE CHARACTERISTICS:
(A) LENGTH: 15 amino acids
(B) TYPE: amino acid
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Human Immunodeficiency Virus Type I
(B) STRAIN: MAL (ix) FEATURE:
(A) NAME/KEY: Peptide
(B) LOCATION: 1..15
(D) OTHER INFORMATION: /label= peptide
/note= "Cytotoxic T lymphocyte immunodominant peptide from envelope glycoprotein from HIV-1 strain MAL; activatible by protease digestion to (ix) FEATURE:
(A) NAME/KEY: Peptide
(B) LOCATION: 4..13
(D) OTHER INFORMATION: /label= peptide
/note= "Highly immunogenic core peptide of immunodominant region of envelope glycoprotein from HIV-I strain MAL."

(xi) SEQUENCE DESCRIPTION: SEQ ID NO:11:

Gly Ile His Phe Gly Pro Gly Gln Ala Leu Tyr Thr Thr Gly Ile
1 5 10 15

(2) INFORMATION FOR SEQ ID NO:12:

(i) SEQUENCE CHARACTERISTICS:
(A) LENGTH: 15 amino acids
(B) TYPE: amino acid
(D) TOPOLOGY: linear (ii) MOLECULE TYPE: peptide (iii) HYPOTHETICAL: NO (v) FRAGMENT TYPE: internal -continued (vi) ORIGINAL SOURCE:
(A) ORGANISM: Human Immunodeficiency Virus Type I
(B) STRAIN: Z6

(ix) FEATURE:
(A) NAME/KEY: Peptide
(B) LOCATION: 1..15
(D) OTHER INFORMATION: /label= peptide
/note= "Cytotoxic T lymphocyte immunodominant peptide from envelope glycoprotein from HIV-1 strain Z6; activatible by protease digestion to (ix) FEATURE:
(A) NAME/KEY: Peptide
(B) LOCATION: 4..13
(D) OTHER INFORMATION: /label= peptide
/note= "Highly immunogenic core peptide of immunodominant region of envelope glycoprotein from HIV-I strain Z6."

(xi) SEQUENCE DESCRIPTION: SEQ ID NO:12:

```
Ser Thr Pro Ile Gly Leu Gly Gln Ala Leu Tyr Thr Thr Arg Gly
1               5                   10                  15
```

(2) INFORMATION FOR SEQ ID NO:13:

(i) SEQUENCE CHARACTERISTICS:
(A) LENGTH: 15 amino acids
(B) TYPE: amino acid
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Human Immunodeficiency Virus Type I
(B) STRAIN: JY1

(ix) FEATURE:
(A) NAME/KEY: Peptide
(B) LOCATION: 1..15
(D) OTHER INFORMATION: /label= peptide
/note= "Cytotoxic T lymphocyte immunodominant peptide from envelope glycoprotein from HIV-1 strain JY1; activatible by protease digestion to (ix) FEATURE:
(A) NAME/KEY: Peptide
(B) LOCATION: 4..13
(D) OTHER INFORMATION: /label= peptide
/note= "Highly immunogenic core peptide of immunodominant region of envelope glycoprotein from HIV-I strain JY1."

(xi) SEQUENCE DESCRIPTION: SEQ ID NO:13:

```
Ser Thr Pro Ile Gly Leu Gly Gln Ala Leu Tyr Thr Thr Arg Ile
1               5                   10                  15
```

(2) INFORMATION FOR SEQ ID NO:14:

(i) SEQUENCE CHARACTERISTICS:
(A) LENGTH: 15 amino acids
(B) TYPE: amino acid
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Human Immunodeficiency Virus Type I -continued (B) STRAIN: ELI (ix) FEATURE:
(A) NAME/KEY: Peptide
(B) LOCATION: 1..15
(D) OTHER INFORMATION: /label= peptide
/note= "Cytotoxic T lymphocyte immunodominant
peptide from envelope glycoprotein from HIV-1
strain ELI; activatible by protease digestion to (ix) FEATURE:
(A) NAME/KEY: Peptide
(B) LOCATION: 4..13
(D) OTHER INFORMATION: /label= peptide
/note= "Highly immunogenic core peptide of
immunodominant region of envelope glycoprotein
from HIV-I strain ELI."

(xi) SEQUENCE DESCRIPTION: SEQ ID NO:14:

```
Arg Thr Pro Thr Gly Leu Gly Gln Ser Leu Tyr Thr Thr Arg Ser
1               5                   10                  15
```

(2) INFORMATION FOR SEQ ID NO:15:

(i) SEQUENCE CHARACTERISTICS:
(A) LENGTH: 16 amino acids
(B) TYPE: amino acid
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Human Immunodeficiency Virus Type I (ix) FEATURE:
(A) NAME/KEY: Peptide
(B) LOCATION: 1..16
(D) OTHER INFORMATION: /label= peptide
/note= "peptide T1, T-cell helper determinant in
HIV-I envelope glycoprote..."

(xi) SEQUENCE DESCRIPTION: SEQ ID NO:15:

```
Lys Gln Ile Ile Asn Met Trp Gln Glu Val Gly Lys Ala Met Tyr Ala
1               5                   10                  15
```

(2) INFORMATION FOR SEQ ID NO:16:

(i) SEQUENCE CHARACTERISTICS:
(A) LENGTH: 15 amino acids
(B) TYPE: amino acid
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Human immunodeficiency Virus Type I (ix) FEATURE:
(A) NAME/KEY: Peptide
(B) LOCATION: 1..15
(D) OTHER INFORMATION: /label= peptide
/note= "peptide HP53, also called TH4.1; helper
T-cell determinant of HIV-1 envelope
glycoprotein."

(xi) SEQUENCE DESCRIPTION: SEQ ID NO:16:

```
Asp Arg Val Ile Glu Val Val Gln Gly Ala Tyr Arg Ala Ile Arg
```

-continued 1 5 10 15

(2) INFORMATION FOR SEQ ID NO:17:

(i) SEQUENCE CHARACTERISTICS:
(A) LENGTH: 10 amino acids
(B) TYPE: amino acid
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: murine cytomegalovirus (ix) FEATURE:
(A) NAME/KEY: Peptide
(B) LOCATION: 1..9
(D) OTHER INFORMATION: /label= peptide
/note= "peptide p18-V-9"

(xi) SEQUENCE DESCRIPTION: SEQ ID NO:17:

Met Tyr Pro His Phe Met Pro Thr Asn Leu
1 5 10

(2) INFORMATION FOR SEQ ID NO:18:

(i) SEQUENCE CHARACTERISTICS:
(A) LENGTH: 11 amino acids
(B) TYPE: amino acid
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: murine cytomegalovirus (xi) SEQUENCE DESCRIPTION: SEQ ID NO:18:

Met Tyr Pro His Phe Met Pro Thr Asn Leu Gly
1 5 10

(2) INFORMATION FOR SEQ ID NO:19:

(i) SEQUENCE CHARACTERISTICS:
(A) LENGTH: 11 amino acids
(B) TYPE: amino acid
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: murine cytomegalovirus (xi) SEQUENCE DESCRIPTION: SEQ ID NO:19:

Tyr Pro His Phe Met Pro Thr Asn Leu Gly Lys
1 5 10

(2) INFORMATION FOR SEQ ID NO:20:

(i) SEQUENCE CHARACTERISTICS:
(A) LENGTH: 13 amino acids
(B) TYPE: amino acid

-continued

```
        (D) TOPOLOGY: linear

   (ii) MOLECULE TYPE: peptide

  (iii) HYPOTHETICAL: NO

    (v) FRAGMENT TYPE: internal

   (vi) ORIGINAL SOURCE:
        (A) ORGANISM: Human Immunodeficiency Virus Type I
        (B) STRAIN: IIIB

   (ix) FEATURE:
        (A) NAME/KEY: Peptide
        (B) LOCATION: 1..13
        (D) OTHER INFORMATION: /label= peptide
             /note= "Active peptide of HIV-I envelope glycoprotein
             from strain IIIB"

      (xi) SEQUENCE DESCRIPTION: SEQ ID NO:20:

    Xaa Ile Gln Arg Gly Pro Gly Arg Ala Phe Val Thr Ile
    1               5                   10
```

POTENT PEPTIDE FOR STIMULATION OF CYTOTOXIC T LYMPHOCYTES SPECIFIC FOR THE HIV-1 ENVELOPE

RELATED APPLICATIONS

This application is a Continuation-In-Part application of the U.S. patent application bearing Ser. No. 07/760,530, filed on Sep. 18, 1991, now U.S. Pat. No. 5,820,865, which is in turn a Continuation-In-Part of U.S. patent application 07/148,692, filed on Jan. 26, 1988 now abandoned. These applications are incorporated in their entirety herein by reference.

BACKGROUND OF THE INVENTION

1. Field of the Invention

The invention relates to peptides useful as vaccines for the prophylaxis and/or treatment of Human Immunodeficiency Virus infection in humans, to compositions incorporating such peptides and to methods for the administration of such vaccines.

2. Related Art

This application makes reference to various literature publications, which are herein incorporated in their entirety by reference.

Live virus vaccines and killed whole or subunit virus vaccines for AIDS have potential safety risks. In contrast, synthetic peptides are inherently safe. Furthermore, molecules corresponding to whole viral proteins but made by recombinant DNA technology contain, in addition to protective epitopes, structures which potentially will elicit suppression of the immune response, or which will elicit antibodies that, rather than being protective, may enhance viral uptake and thus be deleterious. A vaccine which contains only selected peptides that elicit the appropriate type of immunity and do not have other deleterious effects should be more effective for a difficult virus such as HIV.

Our previous work showed that the major CTL antigenic determinant of HIV-1 envelope protein gp160 consisted of residues 315–329 in the numbering sequence of Ratner et al. (27), However, we have now found that this peptide does not bind intact to the class I MHC molecule that must present it to CTL, but rather it must first be proteolytically cleaved, by proteases such as those present in serum.

T-cell stimulation by the HIV-1 gp160 -derived p18 peptide presently by H-2$D^d$ class I major histocompatibility complex (MHC) molecules in a cell-free system was found to require proteolytic cleavage. This extracellular processing was mediated by peptidases present in fetal calf serum (FCS). In vitro processing of p18 resulted in a distinct reverse phase HPLC profile, from which a biologically active product was isolated and sequenced. This peptide processing can be specifically blocked by the angiotensin converting enzyme (ACE) inhibitor captopril and can occur by exposing p18 to purified ACE. The ablity of naturally occurring extracellular proteases to convert inactive peptides to T-cell antigens has important implications for understanding cytotoxic T-lymphocyte (CTL) responses in vivo and for rational peptide vaccine design.

Although naturally processed peptides associate with newly formed MHC class I molecules intracellularly (1), extracellular loading of surface class I molecules by synthetic peptides (2) is commonly used to analyze MHC class I peptide interactions. Recent data have provided substantial evidence that peptides bound to class I are approximately nine amino-acids in length (3–9), but larger peptides are capable of sensitizing targets for class I MHC-restricted lysis. In some cases the activity of these longer peptides can be traced to the prsence of contaminating shorter products which are extremely biologically potent (9).

The HIV-1 (IIIB) gp160 envelope glycoprotein-derived peptide, p18, is 15 amino acids in length (residues 315–329). It is the immunodominant CTL determinant of gp160 in H-2$D^d$ mice (10,11) and can sensitize syngeneic cells for lysis by CTL from HIV-1-infected humans (12).

If a person suspected of being exposed to AIDS is tested for antibodies to HIV and is determined to be seronegative, it is still possible that that person is carrying the virus but has not made antibodies, because a certain percentage of exposed individuals do not develop antibodies for a significant period of time after exposure, and some may never develop antibodies. Nevertheless, that person may have developed a cell-mediated immune response in the form of CTL specific for the envelope of the virus. Because that person's CTL are specific not only for the virus but also for that individual's major histocompatibility complex (MHC) antigens, it is not possible to test for these on transfected tumor targets as was done in the case of the mice, unless one is lucky enough to have transfected tumor that shares MHC (HLA) molecules with the individual to be tested. Because there are so many human HLA types, it is not feasible to have transfected cells of every type available. Although it is possible to produce a transformed tumor line from the individual and transfect it with HIV genes, this is a very difficult, time consuming, laborious process and would not be feasible to do for large numbers of people. Infecting the individual's cells with HIV requires the appropriate cell type that can be infected, and would be hazardous for laboratory workers to handle the concentrated virus. Use of the vaccinia recombinant described above may give many false positive results since most individuals in the U.S. born before 1972 were immunized with vaccinia as a smallpox vaccination, and so would have vaccinia-specific CTL. Purified proteins are generally not taken up by cells in such a way as to make them targets for CTL. However, small peptides such as P18 IIIB (earlier called Env-$K_1$) are capable of sensitizing targets for CTL, as we have shown herein above. Therefore, it would be relatively simple to use P18 IIIB as a diagnostic reagent to test for the presence of HIV-specific CTL in the peripheral blood of an individual. This can be achieved by standard procedures; first, produce PHA or ConA blasts of the peripheral blood lymphocytes of the individual to be tested, label these with $^{51}Cr$ as indicated herein above, incubate these with the peptide P18 IIIB under standard culture conditions similar to those given herein above, but modified for human CTL assays, and add fresh peripheral blood lymphocytes from the same individual. After about 6 hours, one measures the amount of $^{51}Cr$ released into the culture medium, and compares this with controls treated identically but without any peptide, or with a control peptide, without any fresh lymphocytes, and with the maximum $^{51}Cr$ release produced by detergent lysis of the target cells. If there is specific release, the individual can be judged to be carrying the HIV virus, even though no antibodies could be detected.

Previous studies of the ability of this peptide to form stimulatory complexes with purified H-2$D^d$ molecules in vitro, indicated that two activities of FCS were required for recognition of p18 by a specific T-cell hybridoma. One activity was that of β2-microglobulin (β2-m) (13, 14–17) and the other activity could be performed by ovalbumin. Most batches of bovine serum albumin (BSA) were unable to replace this β2-m independent effect of FCS.

We have tested 9, 10 and 11 residue peptides, derived from p18, overlapping or contained within the p18-I-10 peptide, including specifically both possible 9 residue peptides contained within p18-I-10, and all of these have been found to be less active than p18-I-10. This finding concerning the importance of length in the activity of peptides presented by MHC class I molecules and the identification of a truncation of p18, p18-1-10 (residues 318–327), with 10 to $10^2$-fold greater potency of T-cell stimulation prompted us to consider the possibility that ovalbumin and FCS were processing p18 to an active, shorter peptide.

Cytotoxic T lymphocytes (CTL) and T helper cells recognize processed antigenic peptides in association with the products of the major histocompatibility complex (MHC) (26–30). Generally, CD8+ CTL are restricted by MHC class I molecules, such as H-2K, -D, -L in mice and HLA-A, -B, -C in humans, presented on the surface of antigen-presenting cells (APC), while CD4+T helper cells (Th) are restricted by MHC class II molecules, such as I-A or I-E in mice and HLA-DR, -DQ or -DP in humans. T cells are able to recognize a wide variety of antigens in the context of relatively few MHC molecules by means of specific T cell receptors (TCR) (31–34). There is no known difference in overall TCR repertoire between CD4+ and CD8+ T cells.

Although it has generally been assumed that there is no reason to expect the same peptides to be presented by both class I and class II MHC molecules, there are a few cases reported in which peptides presented by class I molecules were found to be presented by or to bind to class II molecules also (35,36). Moreover, we have recently found that the immunodominant antigenic determinant of HIV-I envelope protein gp160 recognized by BALB/c murine as well as human CD8+ CTL with class I MHC molecules (peptide P18IIIB, residues 315–329, RIQRGPGRAFVTIGK, SEQ. ID. NO. 1) (37,38), is also presented by class II MHC molecules of both mice (39) and humans (40) to CD4+ helper T cells. Conversely, we found that three other peptides of HIV-1 gp160 that were originally identified as stimulating CD4+ helper T cells of mice (41,42) and humans (40,43) also were presented by human class I molecules to human CD8+ CTL (38). Thus, we asked whether these latter peptides also were presented by murine class I molecules to CD8+ CTL, and if so, what range of class I molecules could present them.

These findings also led us to raise a related but distinct question. A few cases have been described of antigenic determinants that happen to be broadly or permissively presented by multiple class II MHC molecules, especially in the case of murine I-E or human DR, in which polymorphism is limited to the beta chain, but the alpha chain is conserved (44,45). However, no similar cases have been studied for presentation by class I MHC molecules, and no analysis of 10 different class I MHC haplotypes as here has previously been reported. Because both domains of the MHC peptide-binding site are polymorphic in class I molecules, exploring permissiveness in class I presentation would be of interest in comparison with class II. Also such widely presented antigenic determinants would clearly be useful for development of synthetic vaccines aimed at a broad outbred population of diverse MHC types. This is especially relevant for HIV-1, because whole virus and even whole envelope protein can elicit deleterious immune responses that can enhance infection or contribute to the development of immune deficiency (reviewed in (46)).

Therefore, for both theoretical and potential practical interest, we explored the breadth of presentation by class I MHC molecules from ten distinct murine MHC haplotypes of both the original CTL determinant peptide P18, and two of the original helper T-cell determinant peptides Tl (428–443, KQIINMWQEVGKAMYA, SEQ. ID. NO. 15), and HP53 (HP53, 834–848, also known as TH4.1, DRVIEVVQGAYRAIR, SEQ. ID. NO. 16). P18 and HP53 were presented by at least 4 different class I MHC molecules in mice immunized with recombinant vaccinia virus transfected with HIV-1 gp160, and Tl was recognized by CD8+ CTL in mice of three MHC haplotypes. Indeed, even the same segments of the peptides are recognized by the several haplotypes. Thus, permissiveness of presentation by class I molecules appears to be at least as great as that reported for presentation by class II molecules, and the extent of overlap between the repertoire of sites presented by class I and the repertoire of sites presented by class II may be much greater than suspected. Also, from a practical point of view, these peptides that are broadly presented by multiple class I as well as class II MHC molecules may be versatile components of a vaccine.

SUMMARY OF THE INVENTION

The invention is defined by the properties of peptides of the immunodominant epitopes of the Human Immunodeficiency Virus (HIV) 160 kilodalton envelope glycoprotein (gp160). The purpose of the invention is to develop a vaccine to prevent AIDS based partly or solely on synthetic or recombinant peptides. Cytotoxic T lymphocytes (CTL) may be a primary means of host defense against HIV. The present invention provides the most potent peptide known to induce cytotoxic T cells specific for HIV-1 gp160 envelope protein, and that can kill cells expressing this envelope protein.

Accordingly, one object of the invention is to provide peptides which provide advantageous immune responses, eliciting cytotoxic T lymphocyte response at concentrations in the range of $10^{-12}$ to $10^{-6}$ M. Preferred embodiments of this aspect of the invention are the ten residue peptides which represent the highly immunogenic regions of the V3 loop of various HIV isolates; RGPGRAFVTI (IIIb isolate, residues 4–13 of SEQ. ID. NO. 1), IGPGRAFYTT (MN isolate, residues 4–13 of SEQ. ID. NO. 2), IGPGRAFYAT (SC isolate, residues 4–13 of SEQ. ID. NO. 4), KGPGRVIYAT (RF isolate, residues 4–13 of SEQ. ID. NO. 3), IGPGRAFHTT (SF2 isolate, residues 4–13 of SEQ. ID. NO. 7), IGPGRTLYAR (NY5 isolate, residues 4–13 of SEQ. ID. NO. 8), LGPGRVWYTT (CDC4 isolate, residues 4–13 of SEQ. ID. NO. 9), IGPGRAFRTR (WMJ2 isolate, residues 4–13 of SEQ. ID. NO. 5).

A second object of the invention is to provide peptides which elicit an immune response characterized by activation of both class I-restricted T lymphocytes and class II-restricted T lymphocytes; class I-restricted T lymphocytes elicit a $CD8^+$ cytotoxic T lymphocyte response, class II-restricted T lymphocytes elicit $CD4^+$ T helper lymphocytes, which play a role in both the production of cytotoxic T lymphocytes and in the production of antibodies by B cells.

A third object of the invention is to provide peptides which are activated by cleavage of the peptide by a protease to produce a more active peptide. Such peptides comprise the residues 315–329 (numbered according to Ratner et al. (25)) of the HIV-1 gp160 envelope protein. Preferred embodiments of this aspect of the invention are peptides RIQRGPGRAFVTIGK (isolate IIIB, SEQ. ID. NO.1), RIHIGPGRAFYTTKN (isolate MN, SEQ. ID. NO. 2), SITKGPGRVIYATGQ (isolate RF, SEQ. ID. NO. 3), SIHIGPGRAFYATGD (isolate SC, SEQ. ID. NO. 4), SLSIGPGRAFRTREI (isolate WMJ-2, SEQ. ID. NO. 5), SISIGPGRAFFATTD (isolate Z321, SEQ. ID. NO. 6), SIYIGPGRAFHTTGR (isolate SF2, SEQ. ID. NO. 7), GIAIGPGRTLYAREK (isolate NY5, SEQ. ID. NO. 8), RVTLGPGRVWYTTGE (isolate CDC4, SEQ. ID. NO. 9), SIRIGPGKVFTAKGG (isolate Z3, SEQ. ID. NO. 10), GIHFGPGQALYTTGI (isolate MAL, SEQ. ID. NO. 11), STPIGLGQALYTTRG (isolate Z6, SEQ. ID. NO. 12), STPIGLGQALYTTRI (isolate JY1, SEQ. ID. NO. 13), and RTPTGLGQSLYTTRS (isolate ELI, SEQ. ID. No. 14) being activated by angiotensin converting enzyme.

Further objects of the invention are to provide compositions including such peptides and to provide methods of treatment and/or prophylaxis of HIV infection in humans which utilize such peptides.

DETAILED DESCRIPTION OF THE INVENTION

Figure 1:
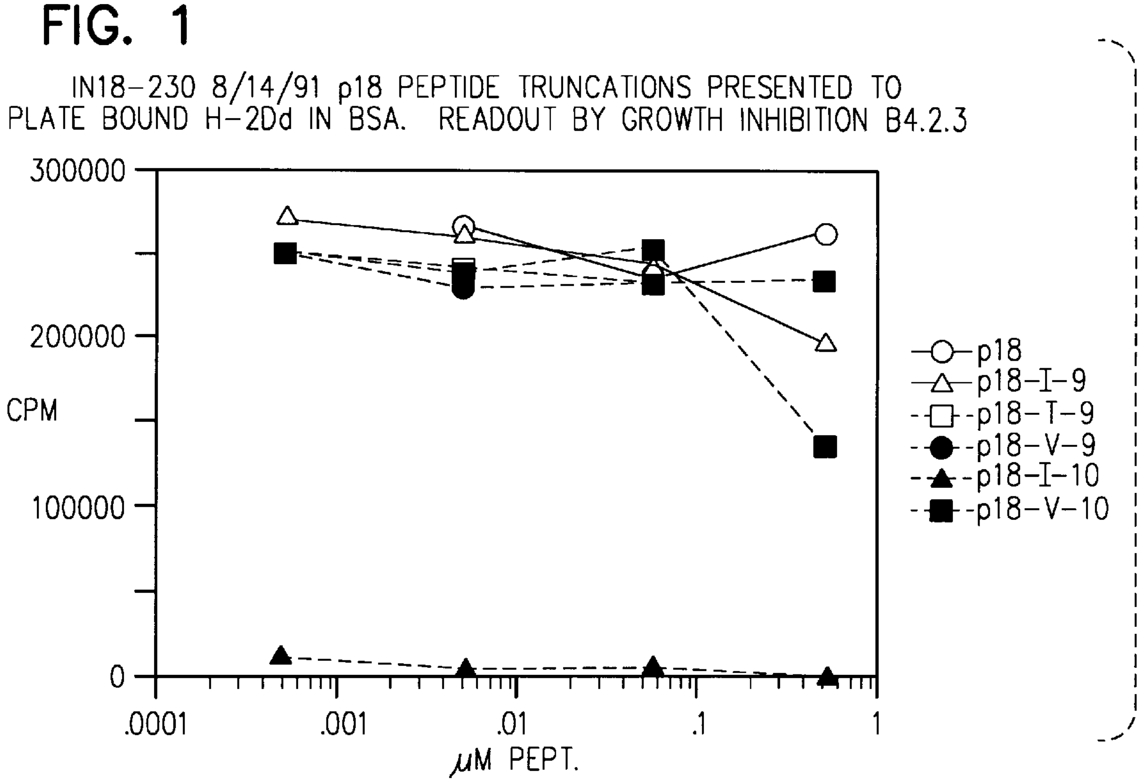
FIG. 1 shows the growth inhibition response of peptide p18 (SEQ. ID. NO. 1) and truncations of that peptide in BSA solution.

Proteolytic cleavage of peptides circulating in vivo is an inefficient process, and therefore therapeutic applications of such peptides requires the administration to a patient of a larger amount of a peptide than if all of the peptide could bind directly to the MHC molecule. The peptide of the present invention overcomes this problem by being able to bind directly to MHC molecules without further proteolysis or other processing, and so we find that in the absence of proteases, it is actually over a million-fold more active than previously described peptides. Even in the presence of serum containing proteases that can process longer peptides, the new invention is still about 10-fold more active than such peptides.

The invention comprises a set of synthetic peptides corresponding to residues 318–327 of HIV-1 strain IIIB gp160 envelope protein in the numbering scheme of Ratner et al. (25), comprising amino acids RGPGRAFVTI (residues 4–13 of SEQ. NO. 1), that we have shown to be highly potent for inducing a cytotoxic T cell response to the HIV-1 envelope protein, and that we have shown does not need processing by proteases. The invention also comprises peptides corresponding to the homologous residues, of other HIV isolates of HIV-1 such as but not limited to the MN isolate (sequence IGPGRAFYTT, SEQ. ID. NO. 2). In this context, "homologous" is defined as the region similar in amino acid sequence and in function in the V3 loop of HIV-I gp160. It includes use of the peptides for immunization in any vehicle, adjuvant, route of administration, or in combination with other material to elicit T-cell immunity, whether for prophylaxis or for immunotherapy of AIDS virus infection.

The general embodiment of the invention is the presentation of a therapeutic peptide to elicit an immune response. It has been found that such peptides are susceptible to degradative processing by proteolytic enzymes. This has either an activating effect, if a large precursor peptide is processed to a smaller, more active product, or a deactivating (inhibitory) effect if a correctly sized peptide is degraded to a small, inactive product. Set forth below are experiments which utilize specific peptides, proteolytic enzymes and inhibitors to assess these processes. These experiments are generalizable in that one may utilize the techniques set forth to examine these processes for any peptide, protease, and inhibitor combination.

Example 2 describes the details of how to assess whether a peptide is a substrate for a proteolytic enzyme by separation of the products of the peptide-protease reaction using High Performance Liquid Chromatography. The isolated products can then be tested for biological activity, if desired, and sequenced to identify any interesting products. Addition of protease inhibitors to the reaction before HPLC separation allows testing for an effective inhibitor. Use of inhibitors specific for particular proteases allows tentative identification of the active protease present in a mixture of proteases.

Example 3 shows a specific example of how a biological assay, rather than HPLC separation, can be used to provide similar information. In Example 3, captopril is used to identify angiotensin converting enzyme as the protease which processes the large MHC class I-binding peptide p18 to the active form p18-I-10. Clearly, different bioassays would be used to assess different sorts of endpoint activities for the peptides, but the general principal illustrated by the experiment remains valid.

The following experimental examples are set forth to illustrate the preferred embodiments of the present invention.

Upon study of these examples, various modifications of the details of the invention will be apparent to one skilled in the art. Such modifications are intended to be within the scope of the invention.

GENERAL METHODS

Mice

H-2-congenic mice on the B10 background and BALB/c mice were purchased from the Jackson Laboratory, Bar Harbor, Me., provided by Drs. D. H. Sachs and R. H. Schwartz of the National Cancer Institute, Bethesda, Md., or bred in our own colony at Biocon, Inc, Rockville, Md. Mice used were 6–18 weeks old.

Recombinant Vaccinia Viruses vSC-8 (recombinant vaccinia virus containing the *Escherichia coli* lacZ gene), and vSC-25 (recombinant vaccina virus expressing the HIV-1 IIIB gp160 envelope glycoprotein without other structural or regulatory proteins of HIV), generous gifts of Dr. Bernard Moss, NIAID, NIH, have been described (47) and were used for immunizing the mice to induce HIV envelope specific CTL.

Peptide Synthesis and Purification

Peptides Tl, P18, and HP53 were prepared under GMP conditions by Peninsula Labs, (Belmont, Calif.) and were single peaks by reverse phase (C18) HPLC in 2 solvents systems. Other peptides were prepared by the multiple simultaneous peptide method of solid-phase peptide synthesis, in polypropylene mesh "tea-bags" as described (48). Peptides were desalted by reverse-phase chromatography on C18 Sep-Pak columns (Waters Associates, Milford, Mass.), and analyzed by HPLC. Some peptides were prepared by an automated peptide synthesizer (model 430A; Applied Biosystems, Inc., Foster City, Calif.) and purified by HPLC.

CTL Generation

Mice were immunized intravenously with $10^7$ PFU of recombinant vaccinia virus. 4–6wk later, immune spleen cells ($5\times10^6$/ml in 24-well culture plates in complete T cell medium (CTM; 1:1 mixture of RPMI 1640 and EHAA medium containing 10% FCS, 2 mM L-glutamine, 100 U/ml penicillin, 100 $\mu$g/ml streptomycin and $5\times10^{-5}$M 2-ME) were restimulated for 6d in vitro with peptides and 10% Con A supernatant-containing medium (rat T cell Monoclone; Collaborative Research, Inc., Bedford, Mass.). Long-term CTL lines were also generated by repetitive stimulation of immune cells with peptide-pulsed irradiated syngenic spleen cells ($2.5\times10^6$ cells/ml; spleen cells were pulsed with peptides at 1–10 $\mu$M for 4 h and then irradiated) in 10% rat Con A supernatant-containing medium.

CTL Assay

Cytolytic activity of in vitro secondary CTL or CTL lines was measured as previously described (37,49) using a 6-h assay with $^{51}$Cr-labelled targets, as indicated in the legends. For testing peptide specificity of CTL, effectors and $^{51}$Cr-labeled targets were mixed with various concentrations of peptide, or effectors were cocultured with peptide-pulsed targets. The percent specific $^{51}$Cr release was calculated as 100× [(experimental release-spontaneous release)/(maximum release-spontaneous release)]. Maximum release was determined from supernatants of cells that were lysed by addition of 5% Triton-X 100. Spontaneous release was determined from targets cells incubated without added effector cells. The 18Neo (H-$2^d$; class I MHC+, class II MHC-neomycin-resistance gene transfected 3T3 fibroblast (37)), L cell (L28; H$2^k$), EL4 thymoma cell (H-$2^b$), and Con A blasts (other haplotypes) were used as targets.

EXAMPLE 1

TESTING THE EFFECT OF PEPTIDE LENGTH ON BINDING TO MHC PROTEINS

We investigated the effect of peptide length on functional bindeng to class I MHC molecules by presenting p18 peptide truncations to plate bound H-2$D^d$ in the presence of BSA. A series of shorter peptides contained within p18 were compared with p18 for the ability to stimulate the growth inhibition of the CTL hybridoma B4.2.3 in BSA solution in the absence of serum.

In this experiment, 0.2 $\mu$g per well soluble H-2$D^d$ protein was coated (13) onto Immulon 4 plates (Dynatech) which were washed and blocked. The sequence of p18 is RIQRGPGRAFVTIGK (SEQ. ID. NO. 1) and of p18-I-10 is RGPGRAFVTI (residues 4–13 of SEQ. ID. NO. 1, FIG. 7). The sequence of p18-I-9 is GPGRAFVTI, p18-T-9 has the sequence RGPGRAFVT (residues 4–12 of SEQ.ID. NO. 1); these two peptides represent the two 9 amino acid overlaps contained within p18-I-10. The two other 9 and 10 residue peptides overlapping p-I-10 that were used were p18-V-9 (QRGPGRAFV, residues 3–11 of SEQ. ID. NO. 1) and p18-V-10 (IQRGPGRAFV, residues 2–11 of SEQ. ID. NO. 1). The peptides are named for the last amino acid residue and the length. Peptide and human β2-microglobulin (Calbiochem)(0.2 $\mu$g per well) were added to the incubation medium, 0.5% BSA (Sigma fraction V) was added to give a final volume of 200 $\mu$l per well and the plates were incubated at 37° C. and 7.5% $CO_2$ for 22–26 h. The plates were then washed twice with PBS and $2\times10^4$ B4.2.3 T-hybridoma cells aded per well in DMEM complete media (13). The plates were incubated from 16–20 h at 37° C. and 7.5% $CO_2$, then pulsed with 1 $\mu$Ci [$^3$H] thymidine (ICN) and collected 4–8 h later for counting the amount of incorporated label to evaluate growth inhibition (18).

In the absence of serum, only the peptide p18-I-10 inhibited the growth of the CTL hybridoma, except at the highest concentration (FIG. 1). Therefore, p18-I-10 is much more than 1000-fold more potent than any of the other shorter peptides, and because the two 9-residue peptides contained within it have much less activity, if any, p18-I-10 is the shortest peptide with optimal activity. This result was completely unanticipated.

Figure 2A:
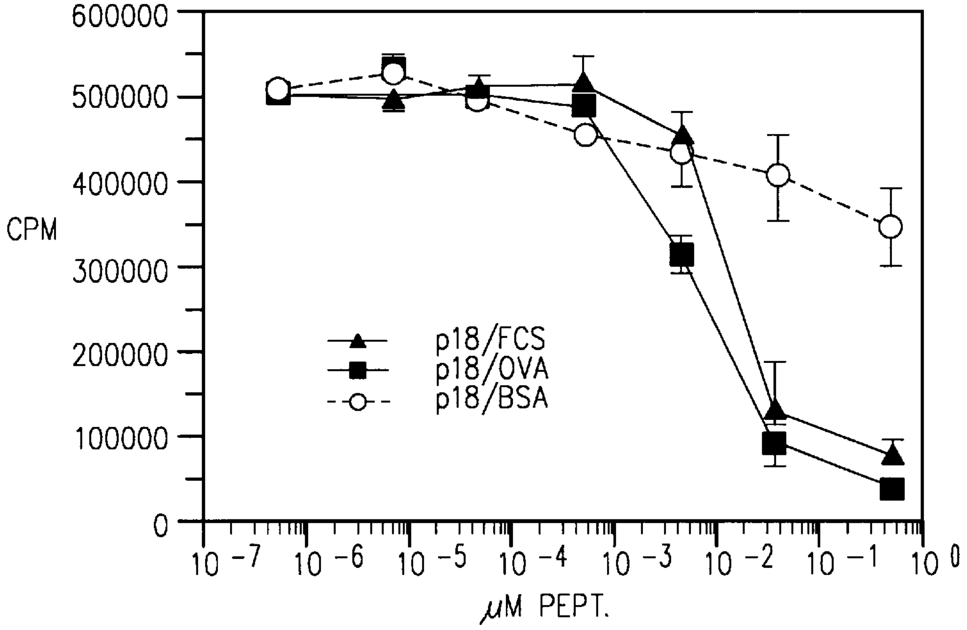
FIGS. 2A–2B show the growth inhibition response to peptide p18 (residues 4–13 of SEQ. ID. NO. 9) or peptide p18-I-10 (SEQ. ID. NO. 1) following treatment with FCS, BSA or ovalbumin. In a, B4.2.3 growth inhibition response to p18 is dependent on ovalbumin or FCS. (- - - ○- - -), p18 in 0.5% BSA; (_□_), p18 in 0.5% ovalbumin; (_▲_), p18 in 0.5% FCS. In b, B4.2.3 growth inhibition response to p18-I-10 is decreased by ovalbumin or FCS. (- - - ●- - -), 18-1-10 in 0.5% BSA; (_■_), 18-1-10 in 0.5% ovalbumin; (_▲_), 18-1-10 in 0.5% FCS.

Next, we compared the two peptides of differing lengths for their functional binding to class I MHC molecules in the presence of BSA, ovalbumin, or FCS (see FIG. 2). This binding was evaluated through activation of the B4.2.3 p18 specific T-cell hybridoma, measured by growth inhibition (18) as described above, except that comparison experiments using 0.5% ovalbumin (Sigma grade V), or FCS (Hyclone) were performed alongside the experiment run in BSA. Results are expressed as c.p.m.±s.e.m. of duplicate samples. In control experiments wherein no peptide was added, the following results were obtained: no peptide in BSA, 475,500 c.p.m.±5710 s.e.m.; no peptide in ovalbumin, 512,800 c.p.m.±34,400 s.e.m.; no peptide in FCS 509,900 c.p.m.±3530 s.e.m. With p18, FCS or ovalbumin was required for significant activation of B4.2.3. In contrast, this activation was decreased by FCS or ovalbumin when p18-I-10 was used. The concentration of p18-I-10 which gave half-maximal stimulation was $10^{-11}$ M when added in BSA. This concentration was 10 to $10^2$-fold less than the half-maximal concentration of p18-I-10 used in FCS and $10^3$-fold lower than the half-maximal concentration of p18-I-10 used in ovalbumin. It was more than $10^6$-fold lower than the half-maximal concentration of p18 used in BSA.

EXAMPLE 2

ANALYSIS OF PROTEOLYTIC ACTIVATION OF PEPTIDE p18 BY SERUM AND BSA

Figure 3A:
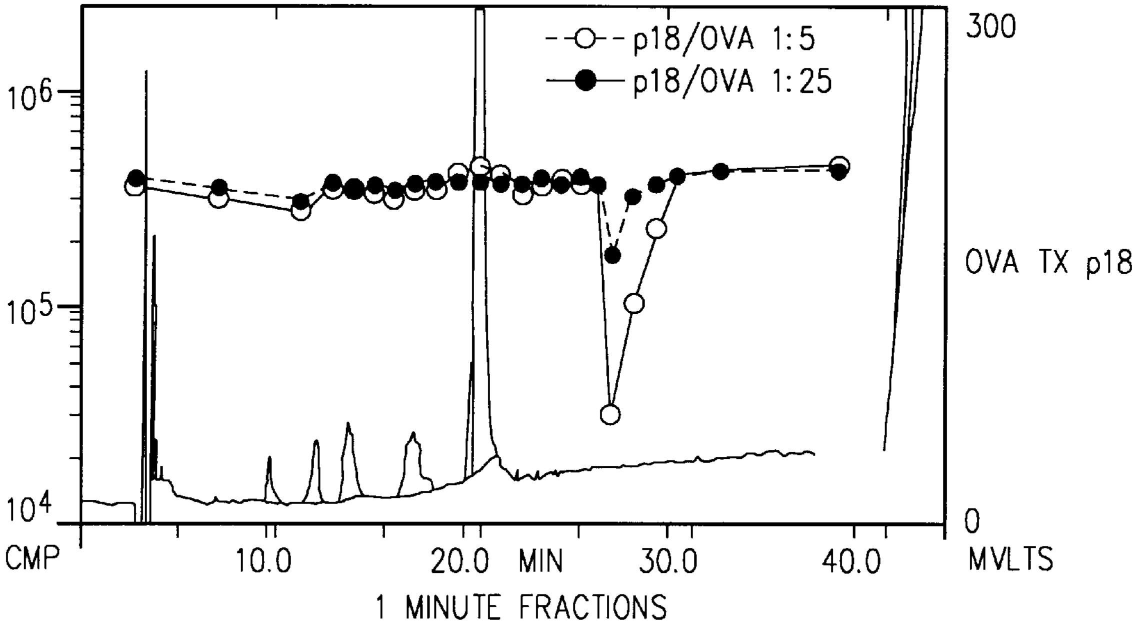
FIG. 3 shows chromatograms of peptides treated with BSA or FCS. In a, reverse phase HPLC fractions of ovalbumin treated p18 and their ability to functionally bind H-2D$^d$. (_____), 220 nm absorbance; (_○_), 1:5 dilution of fractions in 0.5% BSA added to H-2D$^d$ coated plates; (_●_), 1:25 dilution of fractions in 0.5% BSA added to H-2D$^d$ coated plates. In b, reverse phase HPLC fractions of BSA treated p18 and their ability to functionally bind H-2D$^d$. (_____), 220 nm absorbance; (_Δ_), 1:5 dilution of fractions in 0.5% BSA added to H-2D$^d$ coated plates; (_▲_), 1:25 dilution of fractions in 0.5% BSA added to H-2D$^d$ coated plates.
Figure 3B:
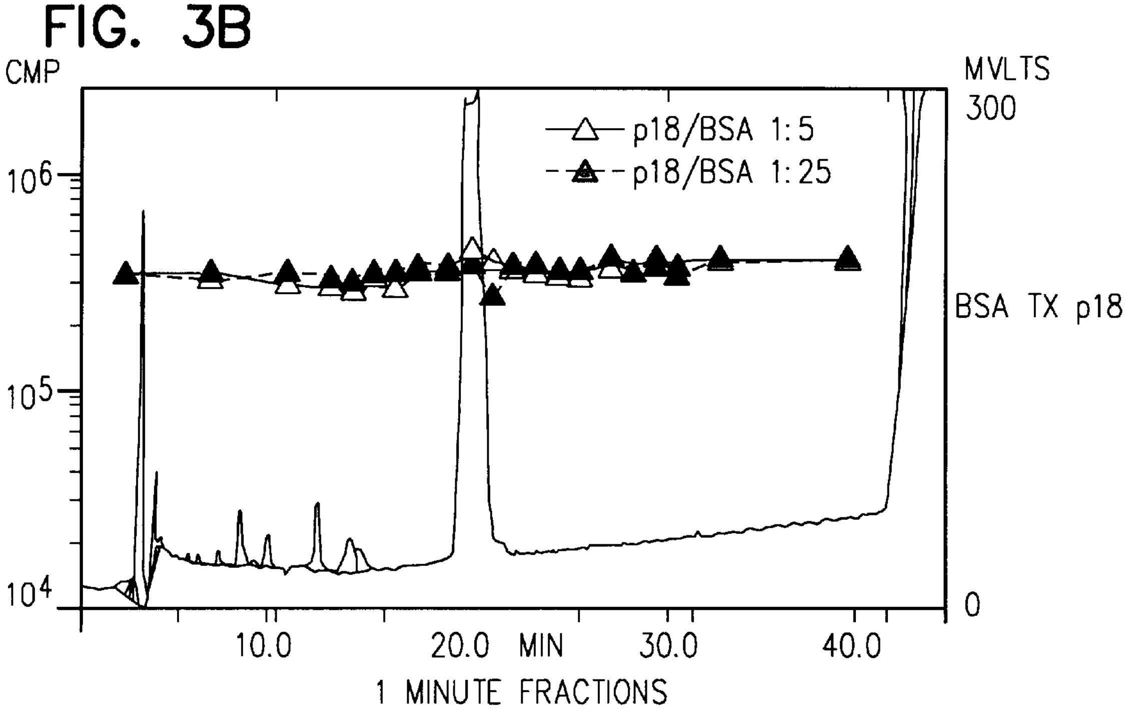

One likely explanation of the results observed in Example 1 is that proteolytic enzymes in ovalbumin and FCS degrade the p18 15-mer to a smaller active form and reduce the active p18-I-10 10-mer to an inactive form. To evaluate this hypothesis we incubated p18 with either ovalbumin or BSA overnight, size fractionated the small MW peptides away from the ovalbumin or BSA, and analyzed them by reverse phase HPLC (FIG. 3).

40 $\mu$l of 2.5 mM p18 was added to 160 $\mu$l 1% ovalbumin or 1% BSA for 15 h at 37° C. 100 $\mu$l of each sample was spun through a Centricon 3 filter (Amicon) into 100 $\mu$l of 1% BSA. The samples were injected into a 4.6 mm×300 mm C18 reverse phase column (Pharmacia), and eluted with a gradient of 15–30% acetronitrile over 30 minutes at a flow rate of 1 ml per min. 40 1 ml fractions were collected, dried down in a Spin-Vac and resuspended in 200 $\mu$l dionized water. 25 $\mu$l of fractions 1–4, 4–8, 9–12, 31–35, and 36–40 were pooled and brought to 200 $\mu$l with 0.1% BSA. 25 $\mu$l of the remaining fractions were brought to 200 $\mu$l with 0.1% BSA. The pooled and unpooled fractions were filter-sterilized and added to H-2$D^d$ (0.1 $\mu$g per well) coated plates at dilutions of 1:5 and 1:25 in the presence of 0.2 $\mu$g per well human β2-microglobulin. After overnight incubation, the plates were washed and B4.2.3 T-hybridoma cells added and assayed for growth inibition as in Example 1. Unpulsed and p18-I-10 pulsed H-2$D^d$ were included as controls. (In FIG. 3*a*) B4.2.3 incorporated 345,000 c.p.m. with H-2$D^d$ incubated with 0.5% BSA. B4.2.3 incorporated 11,900 c.p.m. with H-2$D^d$ incubated with 0.05 $\mu$M 18-1-10 in 0.5% BSA. (In FIG. 3*b*) B4.2.3 incorporated 384,000 c.p.m. with H-2$D^d$ incubated with 0.5% BSA. B4.2.3 incorporated 9649 c.p.m. with H-2$D^d$ incubated with 0.05 $\mu$M 18-1-10 in 0.5% BSA.

A decrease in the amount and a slight increase of the retention time of the major peak of p18 in PBS was seen in the ovalbumin-treated peptide but not in the BSA-treated peptide. The HPLC profile of the ovalbumin-treated p18 also differed from the BSA-treated p18 in amount and retention times of several minor peaks. To determine in which fractions of the ovalbumin-treated p18 the T-cell stimulatory activity eluted, the fractions were assayed for presentation by plate-bound H-2$D^d$. The active growth-inhibiting material was in fractions 26 and 27, eluting later than the p18 major peak; these fractions had very little 220 nm absorbance. The BSA-treated p18 fractions were unable to inhibit the growth of the T-cell hybridoma. This observation suggested that a very small proportion of the FCS or ovalbumin processed p18 was a highly active peptide as has been noted for the SV12 peptide and its synthetic contaminants (9). However, in contrast to the latter case, this active peptide is not a contaminant of the original p18 preparation. The active fractions were pooled. Fractions recovered from the HPLC were subjected to automated Edman degradation on an Applied Biosystems model 470A sequenator, and fractions were identified by amino acid analysis on a model 120A PTH analyzer. FCS treatment of p18 generated similar changes in the HPLC profile (active fractions 24–26), but a clear sequence was difficult to obtain, probably due to a more complex proteolytic system and contaminating serum peptides. The reverse phase HPLC profile of untreated p18 is similar to the profile of BSA treated p18 (major peak BSA-p18 elutes at 19.5 min; major peak p18 elutes at 19.7 min; major peak OVA-p18 elutes at 20.3 min.). The sequence of the active peptide was determined to be, XIARGPGRAFVTI (SEQ. ID. NO. 20) which is identical to p18 lacking two C-terminal residues and possessing the same C-terminus as p18-1-10. The activity in the ovalbumin appeared to be that of a carboxypeptidase, removing the two C-terminal residues from p18.

EXAMPLE 3

DETERMINATION OF THE CARBOXYPEPTIDASE ACTIVITY IN SERUM WHICH ACTIVATES PEPTIDE p18

To identify the carboxypeptidase that processes p18 in FCS, we titrated four carboxypeptidase inhibitors into p18 FCS mixtures, adding them to plate-bound H-2$D^d$. The inhibitors used were potato carboxypeptidase inhibitor (19) which blocks tissue carboxypeptidases A and B, Plummer's inhibitor (20) which blocks carboxypeptidase N (serum carboxypeptidase B), captopril (21) which blocks angiotensin converting enzyme (ACE or peptidyl dipeptidase A), and E-64 (22) which blocks cathepsin B (peptidyl dipeptidase B).

Figure 4A:
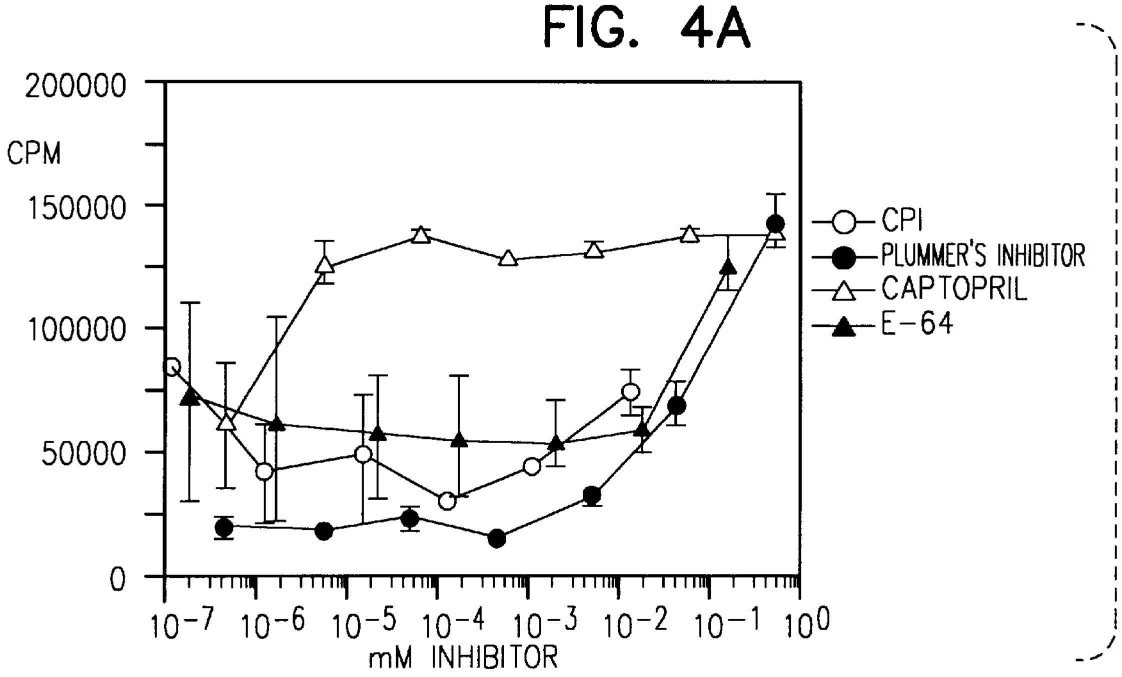
FIGS. 4A–4B show the effect of carboxypeptidase inhibitors on p18 functional binding to H-2$^d$ expressing cells. In a, effect of carboxypeptidase inhibitors in p18 functional binding to H-2D$^d$ on FCS. (_○_), potato carboxypeptidase inhibitor; (_●_), Plummer's inhibitor; (-Δ_), captopril (_▲_), E-64. In b, Angiotensin converting enzyme (ACE) processes p18 into an active form in BSA. (_○_), p18+ACE; (_○_), p18-I-10+ACE; (_Δ_), p18+carboxypeptidase N; (_▲_), 18-1-10+carboxypeptidase N.

The carboxypeptidase inhibitors were titrated as shown in FIG. 4*a*. An Immulon 4 plate with 0.25 $\mu$g per well H-2$D^d$. 0.2 $\mu$g per well human β2-microglobulin and p18 to give a final concentration of 1 $\mu$M were added. The incubation medium was 0.5% FCS. After an overnight incubation B4.2.3 T-hybridoma cells were added and growth inhibition assessed as described in Example 1. Captopril (Sigma) and potato carboxypeptidase inhibitor (Calbiochem) were dissolved in PBS. Plummer's inhibitor (Calbiochem) was dissolved in acidified deionized water. E-64 (Calbiochem) was dissolved in 33% DMSO (<1.7% DMSO at highest concentration in experimental wells). The experiment was done in triplicate and results are shown ±s.e.m.. In control experiments, B4.2.3 thymidine incorporation was measured in the absence of peptide and in the absence of inhibitors: no peptide in FCS 145,000 c.p.m.±11,200 s.e.m.; 1 $\mu$M p18 in FCS 27,800 c.p.m.±4,400 s.e.m.; no peptide in BSA 145,000 c.p.m.±7000 s.e.m.; 1 $\mu$M p18 in BSA 146,000 c.p.m.±1,600 s.e.m.

Figure 4B:
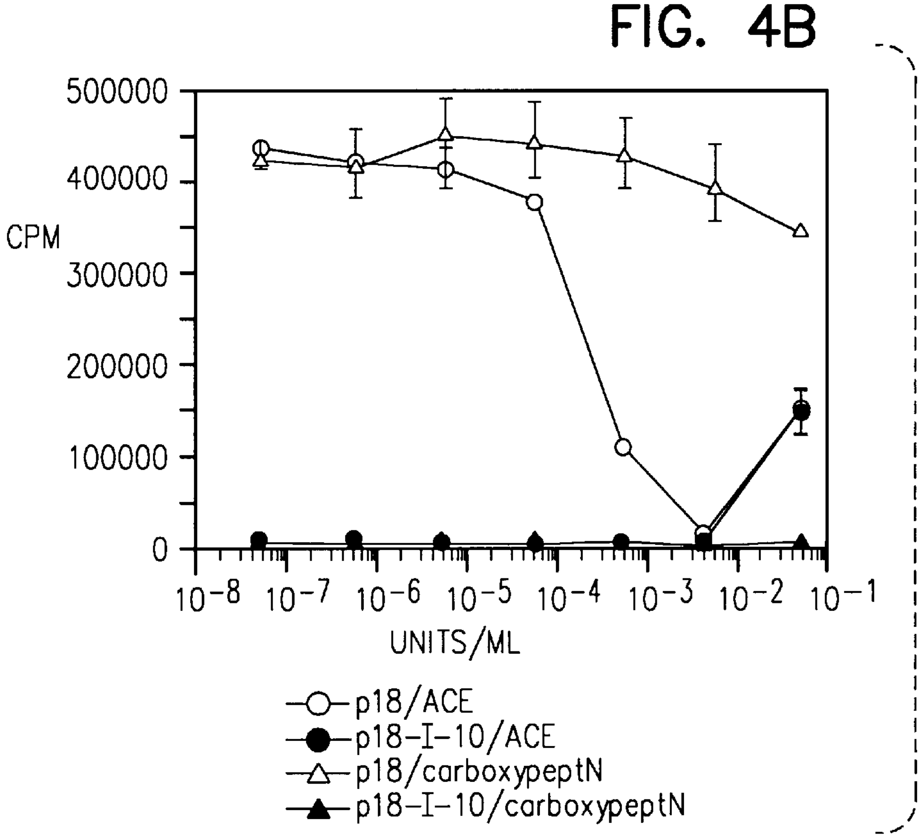

In the presence of FCS, nanomolar concentrations of captopril blocked p18 dependent stimulation of B4.2.3. (FIG. 4*a*). The blocking of FCS processing of p18 occurred at captopril concentrations $10^4$ to $10^5$-fold lower than that of any of the other carboxypeptidase inhibitors. This result suggested ACE (23,24) as a major serum processor of p18. Thus, we attempted to process p18 in the absence of serum or ovalbumin using rabbit lung ACE (FIG. 4*b*).

Carboxypeptidase N (Calbiochem) and ACE (Sigma) were diluted in PBS and titrated as shown in an Immulon 4 plate with 0.1 μg per well H-$2D^d$. The incubation media was 0.5% BSA. After an overnight incubation B4.2.3 T-hybridoma cells were added and growth inhibition assessed as in Example 1. The experiment was done in triplicate and results are shown ±s.e.m. The results of the control experiments were: B4.2.3 thymidine incorporation without carboxypeptidases: No peptide in FCS 429,600 c.p.m.±21,000 s.e.m.; No peptide in BSA 411,800 c.p.m.±29,200 s.e.m.; 1 μM p18 in FCS 112,600±13,200 s.e.m.; 1 μM p18 in BSA 449,600 c.p.m.±21,600 s.e.m.; 0.1 μM p18-I-10 in FCS 13,100 c.p.m.±1,000 s.e.m.; 0.1 μM p18-I-10 in BSA 5,500 c.p.m.±120 s.e.m.

The purified ACE was able to process p18 without serum, whereas human carboxypeptidase N was unable to do so. ACE was not required for T-cell hybridoma stimulation by p18-I-10 and had some inhibitory effect at high concentrations using both p18 and p18-I-10.

EXAMPLE 4

THE INFLUENCE OF ACE PROCESSING ON THE BINDING OF p18 TO ANTIGEN-PRESENTING CELLS

An experiment was performed to evaluate whether the role of ACE in processing p18 observed in the cell-free system described in Examples 1–3 would also apply to cell-surface class I molecules. This experiment was done using H-$2D^d$ transfected L-cells as the antigen presenting cells. In this experiment hybridoma stimulation is indicated by increased thymidine incorporation of the CTLL-2 cells as opposed to decreased thymidine incorporation of the hybridoma cells themselves used to indicate stimulation in the prior experiments.

96-well tissue culture plates (Costar) were blocked with DMEM complete medium. Captopril, Plummer's inhibitor, or no carboxypeptidase inhibitor was added to give a final concentration of $10^{-5}$ M and peptide (p18 or P18-I-10) was titrated. $10^4$ B4.2.3 T-hybridoma cells and $2\times10^4$ H-$2D^d$ positive L-cells were added to each well. After an overnight incubation, 50 μl per well of supernatant was harvested and freeze-thawed. These supernatants were added to $4\times10^3$ CTLL-2 cells in RPMI complete medium to give a final volume of 200 μl per well. After an 18 h incubation 1 μCi[$^3$H] thymidine was added to each well. 4 h later the CTLL-2 cells were collected and counted for incorporated thymidine. Results are shown as triplicates ±s.e.m.

Figure 5A:
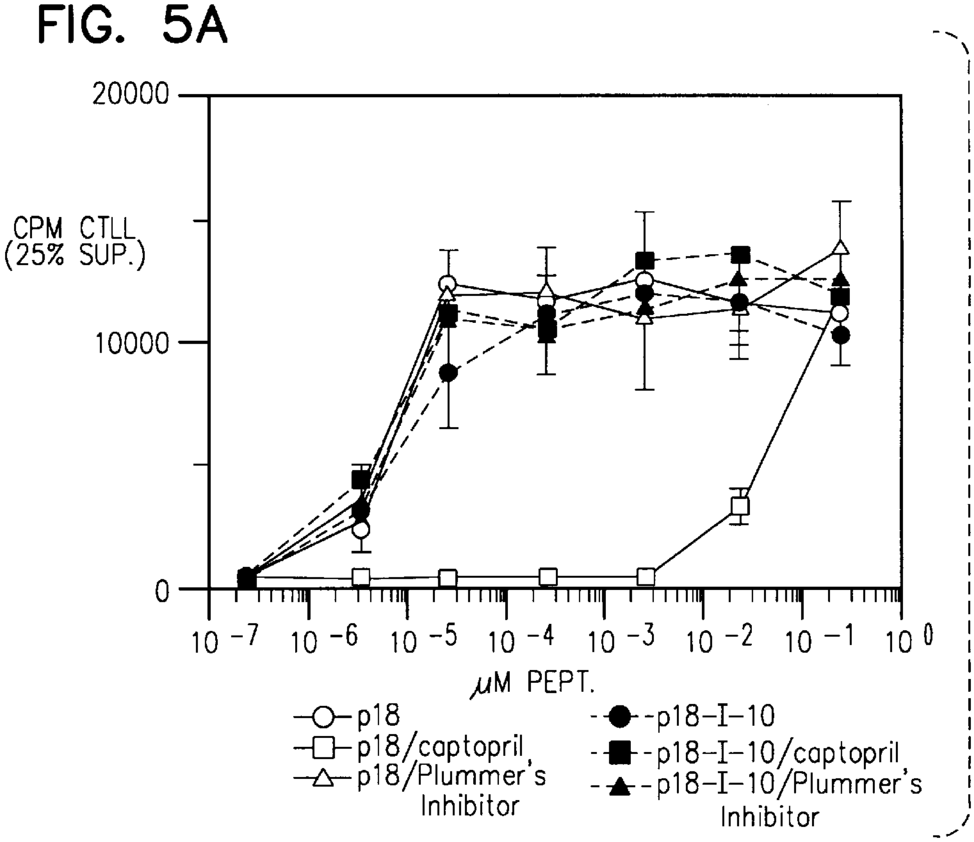
FIG. 5*a*. shows that B4.2.3 lymphokine response to p18 and H-2D$^d$ positive L-cells in FCS is decreased by captopril. (_○_), p18; (_□_), p18+captopril; (_Δ_), p18+Plummer's inhibitor; (_●_), p18-I-10; (- - - ■- - -), p18-I-10+captopril; (- - - ▲- - -), p18-I-10+Plummer's inhibitor. In 5b, The B4.2.3 lymphokine response to gp-160 transfected H-2D$^d$ positive 3T3 cells is not decreased by captopril. (_O_), gp-160 transfectant; (_□_), gp-160 transfectant+captopril; (_Δ_), gp-160 transfectant+Plummer's inhibitor, (- - - ○- - -), Neo transfectant. CTLL-2 thymidine incorporation in the absence of transfected L-cells was <500 c.p.m.

CTLL-2 thymidine incorporation in the absence of peptide was <600 c.p.m.. Peptide p18 and p18-I-10 were titrated in the presence of $10^{-5}$ M captopril or Plummer's inhibitor in the presence of medium containing FCS (FIG. 5*a*). Lymphokine production was used to assess T-cell stimulation in the following experiments, avoiding confusion from thymidine uptake by the presenting cells in evaluating T-cell growth inhibition. The p18 concentration required for half-maximal lymphokine production by the hybridoma was increased by $10^3$ to $10^4$-fold in the presence of captopril. In contrast, stimulation by p18-I-10 was completely insensitive to inhibition by captopril.

To assess the role of ACE in peptide activation when the antigen is endogenous to the cell, the stimulation of the B4.2.3 hybridoma when both the gp160 and H-$2D^d$ are expressed by a transfected fibroblast was tested.

Figure 5B:
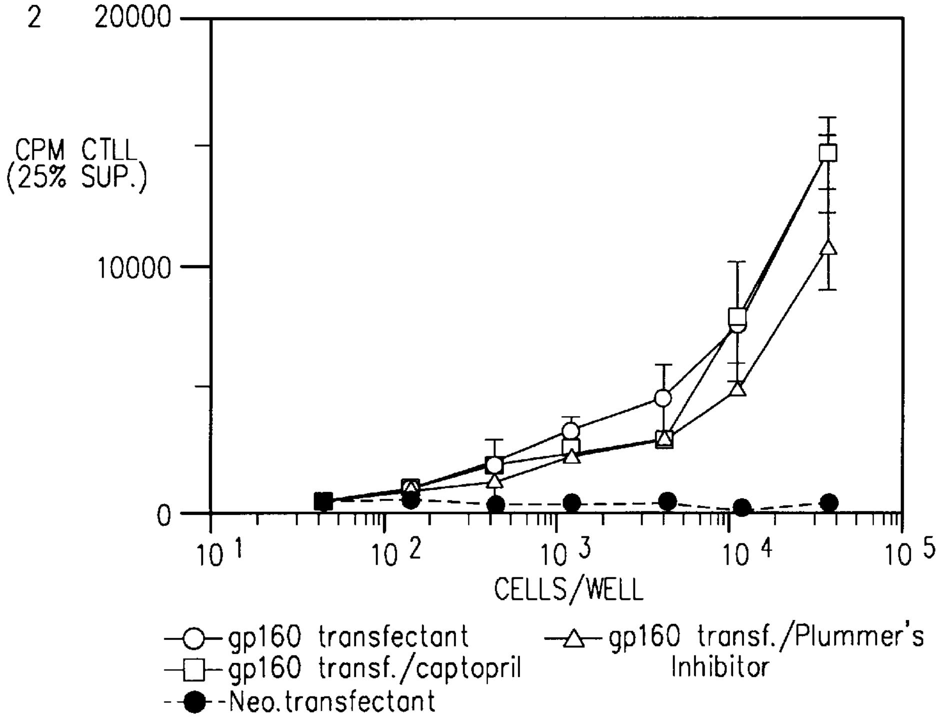

96-well tissue culture plates (Costar) were blocked with DMEM complete medium as before. Captopril, Plummer's inhibitor, or no carboxypeptidase inhibitor was added to give a final concentration of $10^{-5}$ M and gp160 transfected H-$2D^d$ positive 3T3 cells were titrated. Neomycin resistance gene transfected 3T3 cells were titrated as a negative control. $10^4$ B4.2.3 cells in DMEM complete media were added per well. After an overnight incubation the supernatants were freeze-thawed and added to CTLL-2 cells as described above in this example. Results are shown as triplicates ±s.e.m. Captopril had no significant effect on stimulation by p18-I-10, excluding a direct cellular effect of captopril, and Plummer's inhibitor and E-64 had no effect on p18. In contrast, stimulation of the B4.2.3 hybridoma is not affected by captopril or Plummer's inhibitor when a transfectant cell (10) that expresses the gp160 envelope protein and H-$2D^d$ is used as the antigen source (FIG. 5*b*).

The data in FIG. 5*a* suggests that the ACE extracellular processing demonstrated in the cell-free system is applicable to the cell-surface system. The data in FIG. 5*b* suggests that the intracellular processing of the antigen is not dependent on an ACE-like activity or occurs in a cellular compartment inaccessible to captopril.

EXAMPLE 5

PROTEOLYTIC ACTIVATION OF PEPTIDES DERIVED FROM CYTOMEGALOVIRUS

To demonstrate that the processing of peptide antigens longer than ten residues by a proteolytic clipping mechanism is a general phenomenon, we investigated the activation of peptides derived from murine cytomegalovirus (MCMV).

MCMV variant peptides were titrated in complete medium (containing FCS) in the presence or absence of $10^{-5}$ M captopril. $2\times10^4$ H-$2L^d$ transfected L cells and $1\times10^4$ E1B6 T cell hybridoma cells (anti-H-$2L^d$+MCMV) were added per well for an overnight incubation. One μCi $^3$H-thymidine was added per well the following day and 4 hrs. later the cells were harvested and the amount of $^3$H-thymidine incorporation was determined. The activation of the E1B6 hybridoma was demonstrated by inhibition of growth.

Figure 6A:
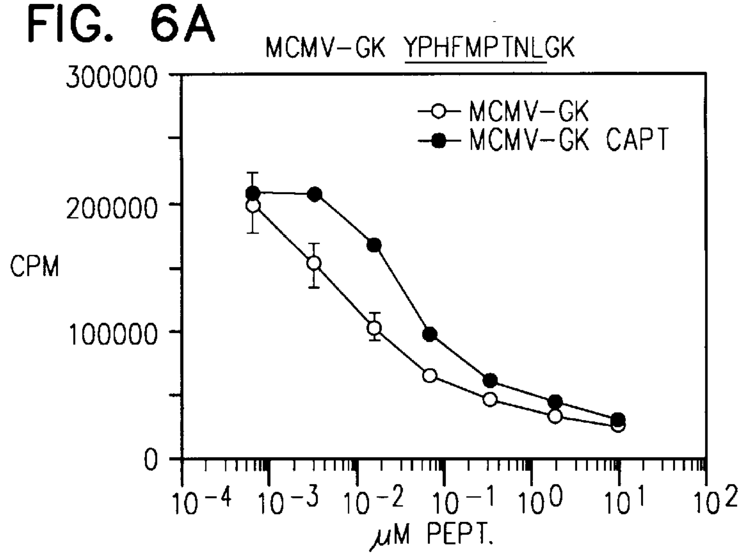
FIG. 6 shows the activation of a murine cytomegalovirus responsive CTL by peptides derived from murine cytomegalovirus when incubated in the presence of FCS with and without captopril.
Figure 6B:
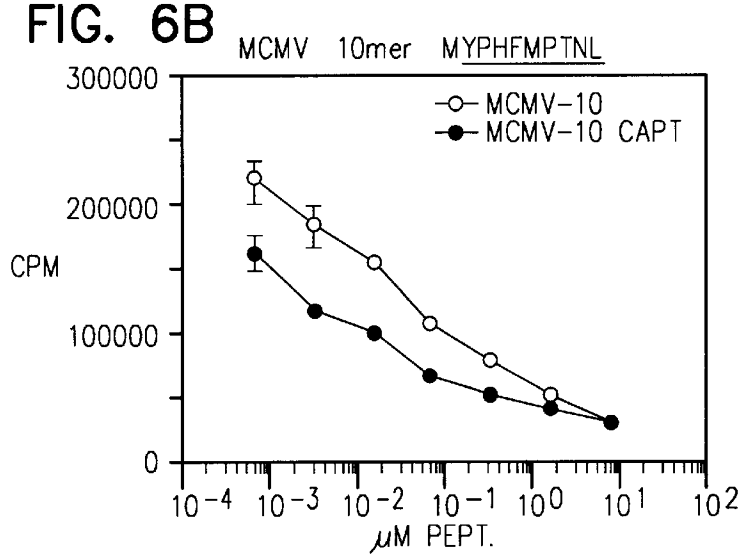
Figure 6C:
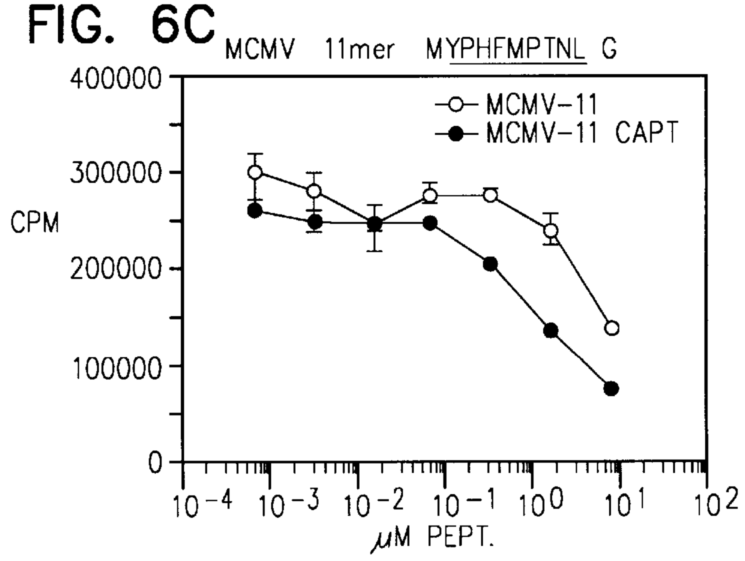
Figure 8A:
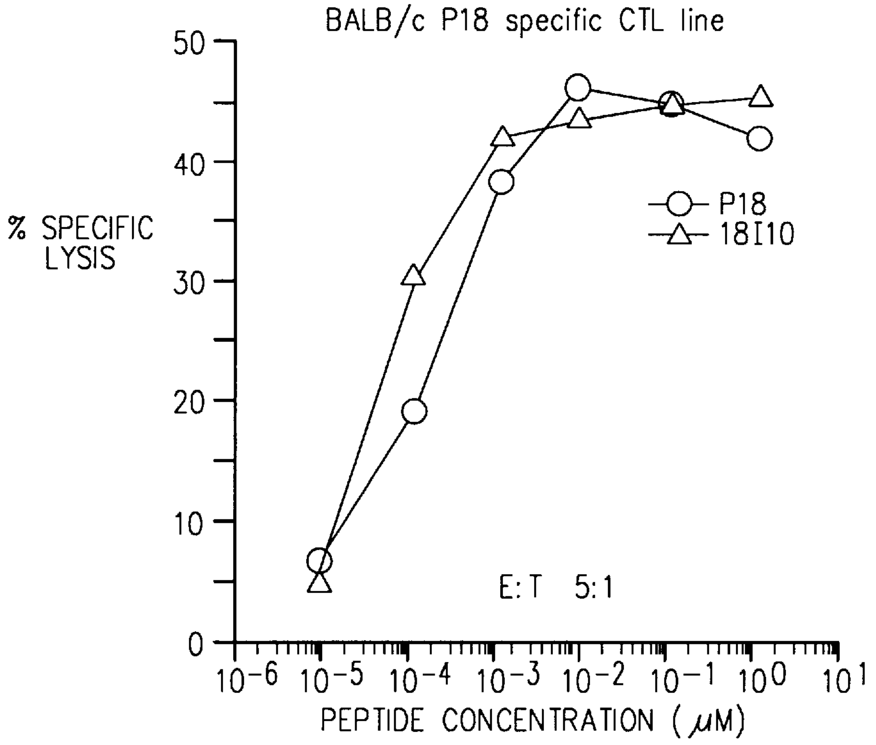
FIG. 8 shows the recognition of the 10-residue core peptide p18-I-10 by cytotoxic T lymphocytes of four different class I MHC types. Effectors from each CTL line were added to $^{51}$Cr-labelled 18Neo (Balb/c 3T3 fibroblasts) and lysis was assessed in the presence of the indicated concentrations of peptides at an effector to target ratio of 5:1.
Figure 8B:
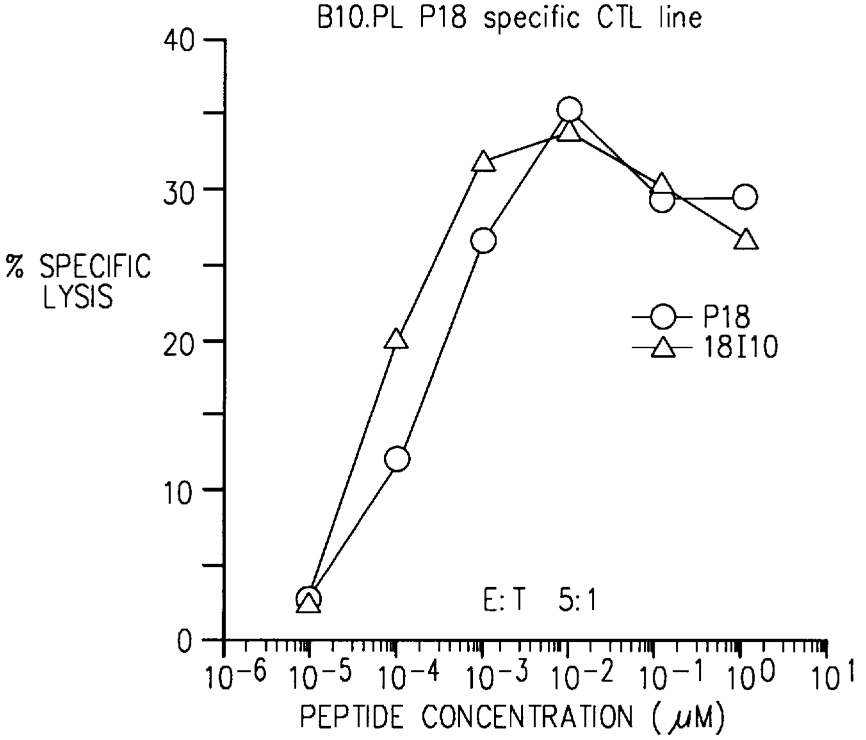
Figure 8C:
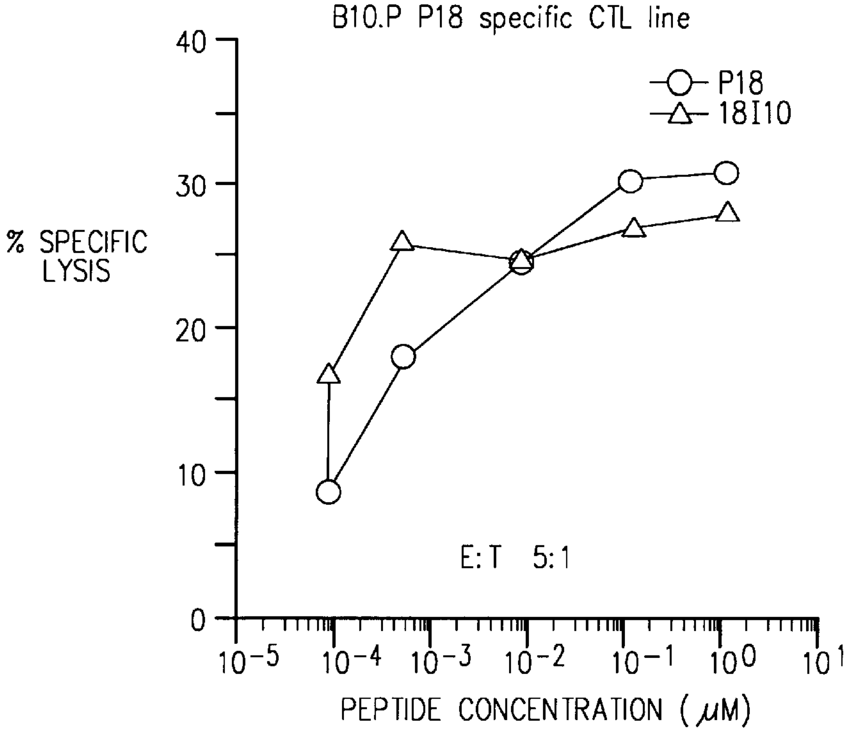
Figure 8D:
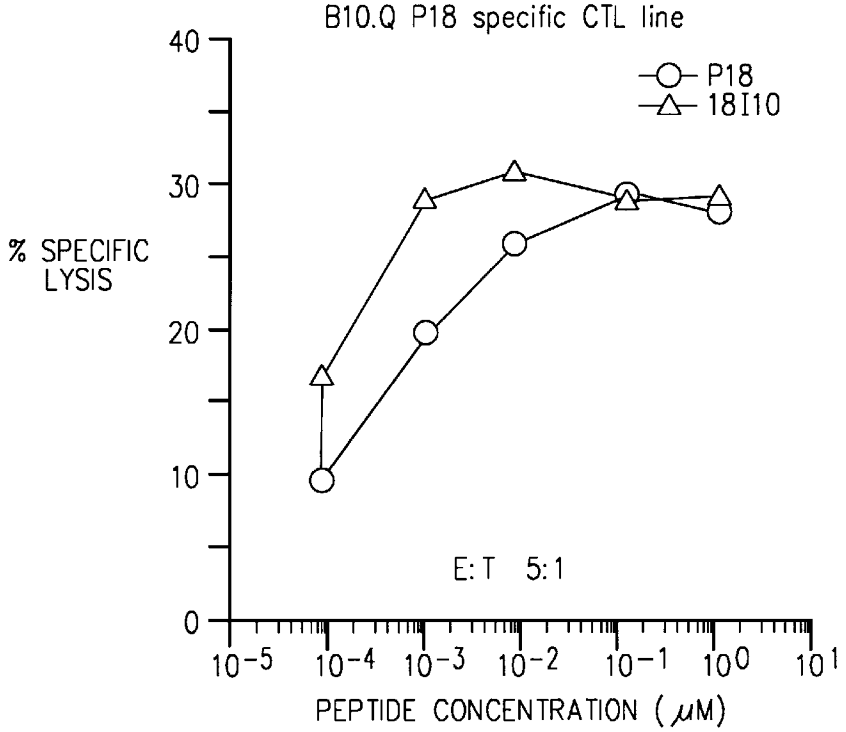

As shown in FIG. 6, both MYPHFMPTNL (SEQ. ID. NO. 18) and MYPHFMPTNLG (SEQ. ID. NO. 18) MCMV peptide variants were enhanced in their ability to stimulate a class I-restricted T cell hybridoma by the ACE inhibitor captopril. The activity of the MCMV peptide YPHFMPTNLGK (SEQ. ID. NO. 19 ) is decreased by an ACE inhibitor in a fashion similar to that observed for peptide p18 as described above. Such a result shows that captopril is useful as an inhibitor of proteolysis of therapeutic peptides. This result also generalizes the effect of ACE to another class I-restricted peptide antigen and clearly demonstrates increased responsiveness of T cells to peptide in the presence of the protease inhibitor captopril.

EXAMPLE 6

FINE SPECIFICITY OF p18-SPECIFIC CTL

Figures 2B, 7:
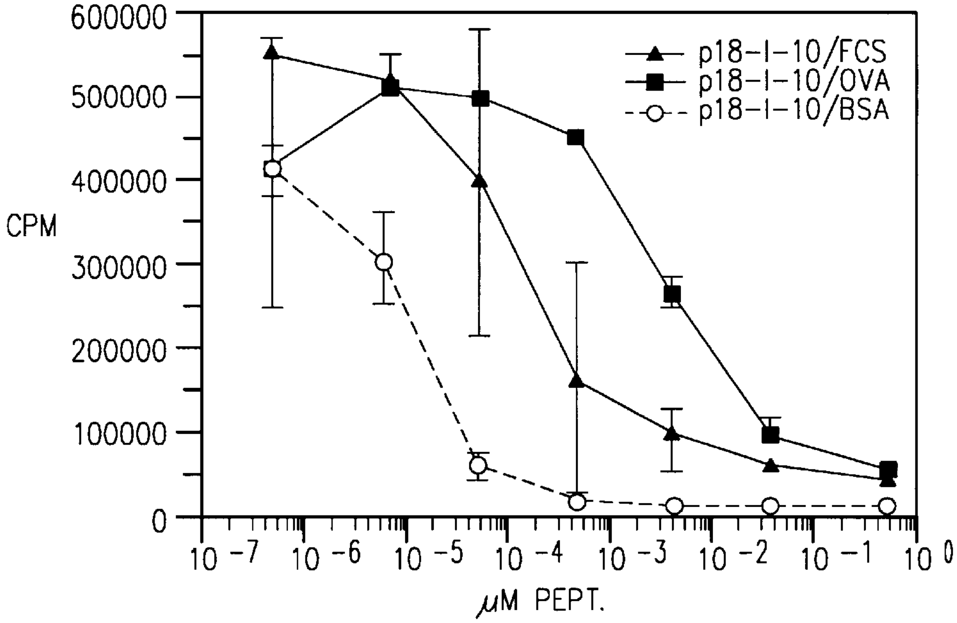
FIG. 7 shows the sequences of the variant forms of the p18 peptide utilized in several experiments.

As previously reported (50), the CTL specific for P18 (18IIIB; HIV-1-IIIB isolate derived) did not crossreactively kill H-$2^d$ targets infected with recombinant vaccinia virus expressing the envelope gene from the natural HIV-1-RF variant, or targets pulsed with a peptide corresponding to the homologous site in the HIV-1-RF gp160 envelope protein. Therefore, by examining the role of each residue at which these variants differ, we could both identify the residues involved in interaction with MHC molecule or TCR and also examine the structural basis for the effect of viral variation on T cell reactivity in the several MHC haplotypes. We synthesized a series of peptides with single amino acid substitutions at positions in which 18IIIB (315–329, RIQRGPGRAFVTIGK, SEQ. ID. NO. 1) and 18RF (315–329ΔΔ TKGPGRVIYATGQ where Δ indicates a deletion, residues 3–15 of SEQ. ID. NO. 3) differ (FIG. 7). Where they were identical an alanine was substituted. Thus, each residue of the 18IIIB sequence was substituted by Δ,Δ,T,K,A,A,A,A,V,I,Y,A,T,A, and Q at positions 1 to 15, respectively, to produce peptides 18-1 through 18-15, respectively. The results are presented in FIG. 8.

As shown previously in the BALB/c strain (50), substitutions at positions 322 (R) (18-8) and 324 (F) (18-10), and 325 (V) (18-11) affected CTL activity. In addition 318 (R) (18-4), 319 (G) (18-5), 320 (P) (18-6), 321 (G) (18-7), 323 (A) (18-9), 326 (T) (18-12), and 327 (I) (18-13) also showed some effect on this CTL line, which was grown by stimulation only with specific peptide 18IIIB but not with the transfectant expressing whole gp160 protein as in the previous study (50). Substitution of 324 (F) with Ile (peptide 18-10) completely abrogated the CTL response of all H-$2^d$-restricted CTL (B10.D2, B10.A, and BALB/c mice) and of H-$2^p$ but not H-$2^u$ and H-$2^q$ CTL. This result indicated that 18-10 can bind to class I MHC molecules of some haplotypes (H-$2^{u\ and\ q}$) even though competition studies showed that it did not bind $D^d$ (50). In B10.D2, using the same class I molecule as BALB/C, the substitution of 319, 321, 322, 323, or 324 completely abrogated the peptide activity. Significant effect was also demonstrated by the substitution of 325, 326, and 327. The reason for the differences from BALB/c is not clear but may reflect difference in the TCR gene repertoire. A few substitutions of the central region of P18 (318, 320, 322, and 327 in B10.PL; 318, 319, 324 and 326 in B10.P) could not sensitize target cells in the B10.PL and B10.P, respectively. Substitutions at 319, 322, 325, 326, and 327 strikingly affected the killing in B10.Q. The subtle differences between the lines were not likely to be due to heterogeneity of CTL in the lines, because titration of all the peptides with CTL clones from B10.D2 and B10.PL gave virtually identical results. However, substitutions in the N-terminal three positions (315–317) and C-terminal two positions (328–329) had much less effect on killing in any of the strains. Thus, although the details of fine specificity were different, it appeared that CTL of all six strains recognized the same core region, residues 318–327.

To further test this conclusion, and based on other observations described in the preceding Examples, a truncated synthetic peptide was synthesized, 18-I-10, consisting of this 10 residue segment, 318–327, and tested for recognition by CTL lines of all four MHC haplotypes (FIG. 8). This 10-residue core peptide was actually found to be more active than the full-length P18 when presented by all four class I molecules. Thus, the moderate effects of substitutions at positions 315–317 and 328–329 must have been due to other effects of flanking residues on peptide conformation or other aspects of recognition. However, the results shown in FIG. 8 clearly indicate that all four class I molecules present the same core 10-residue sequence.

To determine if the same or overlapping sites within P18 are presented with the different class I MHC molecules, we used naturally occurring substitutions within this area, which is in the hypervariable region of gp160. There is no cross-reactive killing between P18IIIB and P18RF. To localize the critical residues of P18 for recognition by CTL of five different MHC haplotypes, we used 15 substituted peptides, each with a single substitution. There was observed some similarity of fine specificity of CTL lines against P18 restricted by different haplotypes. The substitutions of 322 (R) by Ala and 324 (F) by Ile markedly reduced the CTL recognition of peptide in BALB/c (H-$2^d$), and the latter substitution (324) appeared to be critical for other CTL lines restricted by $D^d$ (B10.D2) and by H-$2^p$ but not for H-$2^u$ and H-$2^q$ restricted CTL lines. In B10.A mice and H-$2^d$ mice, substitution of residue 325 (V) also strikingly abrogated the activity of P18. The substitutions of 319 and the residues between 321 and 326 were important for P18 to be presented to the CTL line of B10.D2. The difference of fine specificity using these substituted peptides between BALB/c, B10.D2 and B10.A therefore suggests differences in TCR structures of CTL lines restricted by $D^d$ class I molecules in these strains. P18 may be presented by the $D^d$ class I MHC molecules to different CTL in a very similar manner, or alternatively, it is possible that the peptide can bind in more than one way to the same MHC molecule (51). In either case, CTL with different TCR would be differentially sensitive to the different substitutions. Although the fine specificity was different from strain to strain, the activity of P18 was less affected by the substitution of the three N-terminal residues (315–317) and the two C-terminal residues (328–329) than the central 10 residues in all six strains. Definition of this 10-residue core was confirmed using a 10-residue peptide, 18-I-10, which was more active than the whole P18 in for recognition by CTL with all four class I molecules. Thus, the different MHC molecules are not simply seeing different adjacent or partially overlapping antigenic determinants within the same peptide. As in the case of HP53, the requirement for the same core region for presentation of P18 by multiple class I MHC molecules indicates that this is a single broadly presented antigenic site and may make this peptide valuable for vaccine development in a broadly MHC diverse population. It also suggests that these core regions of these two peptides have a predilection to bind to class I MHC molecules in general, accounting for the widespread recognition of these peptides.

EXAMPLE 7

SURVEY OF MHC CLASS I MOLECULES PRESENTING SPECIFIC PEPTIDES TO CTL LINES IN H-$2^d$ STRAINS

Based on the experimental data using L cell transfectants expressing $D^d/L^d$ class I molecules, a previous study (50) demonstrated that P18 is seen in H-$2^d$ mice only with the class I molecule $D^d$ and that the α1 and α2 domains of $D^d$ were both necessary and sufficient in the context of an intact class I molecule. In this study, we used transfectants expressing $K^d$, $D^d$, or $L^d$ molecules to determine which molecule was specifically required for the presentation of P18 and HP53 in H-$2^d$ and H-$2^a$ strains. The targets were pulsed with the indicated peptide and labeled with $^{51}$Cr at same time. T37.2.1 (α1α2 of $D^d$) and T4.8.3 ($D^d$) were found to present HP53 as well as P18. Any other $D^d/L^d$ exon-shuffled transfectant targets were not sensitized with these peptides. Therefore both α1 and α2 domain were necessary and together sufficient to present these peptides. The $K^d$ molecule also presented P18 to a very small population of CTL in BALB/c but not in B10.D2 or B10.A mice. In B10.Q, we also used well-defined recombinant mice, B10.AKM (H-$2^m$, $K^k/D^q$) and B10.T(6R) (H-$2^{y2}$, $K^q/D^d$), to map the restriction element in the H-$2^q$ haplotype. The results demonstrated that $D^q$ (or $L^q$) but not $K^q$ could present both P18 and HP53 to H-$2^q$ CTL.

We were able to map the restriction in the H-$2^{d\ and\ a}$ and H-$2^q$ haplotypes to $D^d$ and $D^q$ (or $L^q$), respectively. Appropriate recombinant mouse strains do not exist to separate $D^q$ and $L^q$ in the H-$2^q$ haplotype or to map the restriction to K or D in the other haplotypes. However because peptides are more frequently presented by more than one allele from the same locus than by MHC molecules of different loci (26,52), it is likely that these peptides are presented by the D molecules of the other haplotypes as well.

To determine whether the response to the immunodominant epitope of the HIV-1-IIIB envelope protein also depends on both the α1 and α2 domains of the $D^d$ class I molecules, we used eight L cell (H-$2^k$) transfectants with different exon shuffles between $D^d$ and $L^{d.}$ The results revealed that the P18 and HP53 peptides required both α1 and α2 domains of the $D^d$ molecule for effective peptide presentation. We found that a small population of P18 specific CTL derived from BALB/c spleen cells immunized with vSC25 vaccinia virus expressing gp160 could also recognize P18 presented by $K^d$ class I molecules to some extent. For the presentation of P18 by $D^{d,}$ two domains α1 and α2 were sufficient and neither the α1 and α2 domain alone was sufficient for the presentation, when the other domains derived from $L^d$. Therefore, both the α1 and α2 domain derived from $D^d$ are necessary and together sufficient, in the context of an intact class I molecule, for the peptide presentation of P18 and HP53. This can be contrasted with examples of peptides broadly presented by class II molecules in which the presenting element, DR or I-E, has a nonpolymorphic alpha chain and only the beta chain is polymorphic, so that the permissiveness could depend on interaction primarily with one side of the MHC peptide-binding groove (44,45).

It is thought that a vaccine eliciting HIV-specific CTL may be protective against HIV, because CTL can block outgowth of HIV in vitro (53,54). Here it was shown that P18 and HP53 from gp160 were found to be presented by four different class I MHC molecules to CTL as well as to helper T cells by class II MHC as previously shown. The broad recognition of these peptides with different classes of MHC molecules as well as different alleles of class I molecules suggests that these peptides could play a versatile role as components of a vaccine for HIV.

EXAMPLE 8

EFFICACY OF THE REGION OF HIV gp160 HOMOLOGOUS TO PEPTIDE p18-I-10 IN ACTIVATION OF CTL

Figure 9:
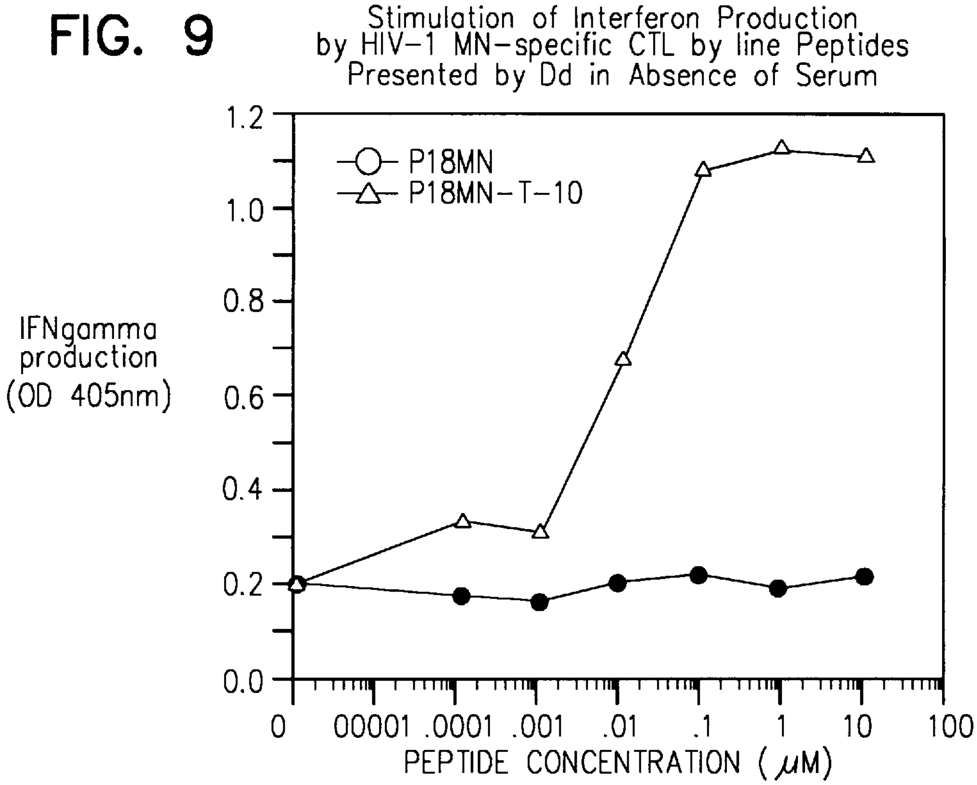
FIG. 9 shows the the interferon production by a HIV-1, strain MN-specifc CTL line in response to presentation of the MN strain peptides homologous to p18 and p18-I-10.

Purified $D^d$ class I MHC molecules were coated onto plastic microtiter wells as described in Example 1, and pulsed with the indicated concentrations of p18MN or p18MN-T-10 (IGPGRAFYTT, residues 4–13 of SEQ. ID. NO. 2) in BSA solution in the absence of serum, as in Example 1. Then, instead of the T-cell hybridoma, cells of an HIV-1 MN-specific CTL line (64) were added and cultured overnight. Culture supernatants were then harvested and tested for interferon-gamma production by ELISA as a measure of CTL activation (FIG. 9). The results clearly show 1) that p18MN-T-10 is the active core of p18MN, exactly homologous to the p18-I-10 active peptide from p18; and 2) in the absence of serum to process the peptides, pp18MN-T-10 is able to bind to the class I molecule and be presented to $CD8^+$ cytotoxic T cells, whereas the 15-mer p18MN is not. Thus, the results with p18-I-10 are generalizable to other strains of HIV-1, such as the MN isolate.

EXAMPLE 9

IL-2 PRODUCTION BY gp160-IMMUNE $CD4^+$ T CELLS STIMULATED BY PEPTIDES p18 AND p18-I-10

To demonstrate that peptides p18 and p18-I-10 would be recognized by class II MHC molecules, the following experiment was performed.

Figure 10:
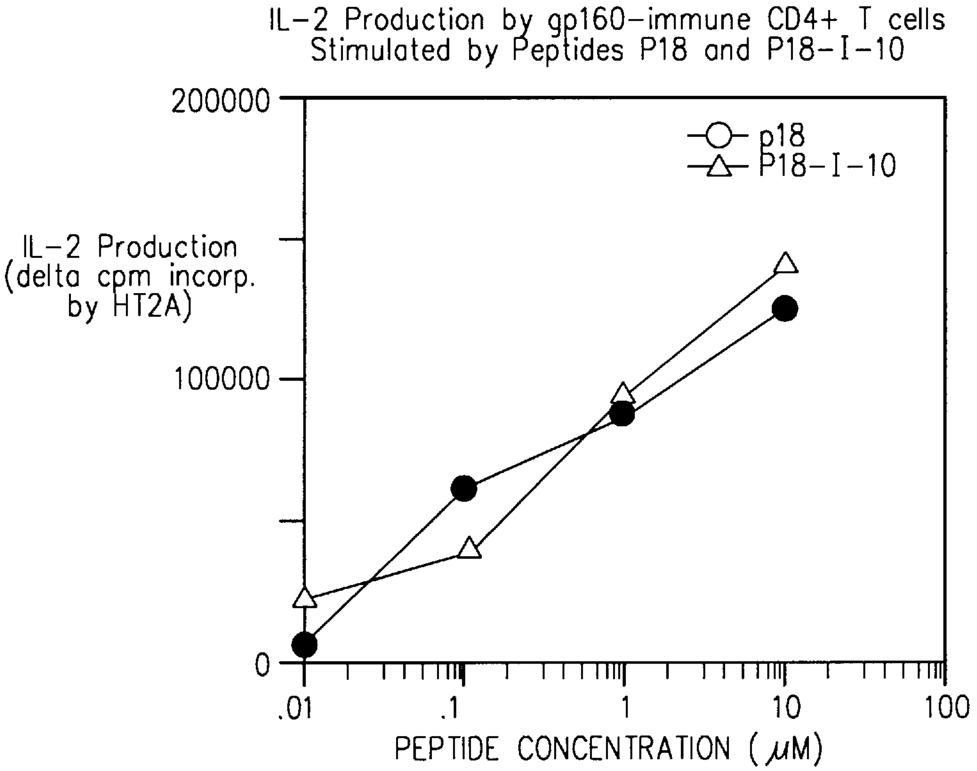
FIG. 10 shows the activation, measured by IL-2 production, of gp160-immune CD4$^+$T cells stimulated by peptides p18 and p18-I-10.

Spleen cells from BALB/c mice immunized with recombinant vaccinia virus expressing HIV-1 IIIB envelope protein gp160 were depleted of $CD8^+$ T cells with anti-CD8 and complement to remove CTL, so that the only cells responding were $CD4^+$ helper T cells. They were then stimulated with peptides p18 or p18-I-10 at varying concentrations shown for 24 hrs. at 37° C., and the culture supernatants were then harvested and tested for IL-2 by the ability to stimulate [$^3$H]-thymidine incorporation by the IL-2 dependent T-cell line HT2A in another 24-hour culture. (FIG. 10). In a control experiment, the response was abrogated by treatment with anti-CD4 antibody.

The data show that p18-I-10 is as potent as the full-length p18 at stimulating IL-2 production. Therefore, this same 10-residue peptide is not only much more potent for stimulating CTL, but is also capable of stimulating helper T cells.

EXAMPLE 10

CHEMICAL MODIFICATION OF THE PEPTIDES TO ENHANCE THEIR PHARMACOLOGIC CHARACTERISTICS

Small peptides circulating in the blood are subject to degradation by proteolytic action and clearing by the kidneys. Yet, a number of naturally occurring peptides are found in the circulation, for example the enkephalins. These small peptides are often found to be modified by amidation of the carboxy-terminus (55,56). Thus, it may prove advantageous to produce chemically modified variants of the peptides for use in therapeutic applications. The enzymatic carboxy-terminal amidation of a synthetic peptide has been described (58,59). Also, the addition of residues useful for the cross-linking of the peptides to carrier proteins for immunizations or to solid supports for immunoassay or antibody purification applications may prove advantageous. Many means for chemical modification of peptides are well known in the art.

The peptides of the instant invention could also be coupled to, or co-synthesized with, peptides that bind to or induce production of neutralizing antibodies to HIV or helper T-cells specific for HIV. Attachment to HIV specific carriers would cause a memory helper T-cell response on exposure to HIV, in contrast to the use of HIV unrelated carriers which would not produce such a memory response on exposure to the virus. Useful HIV specific carriers are, for example; as described in Cease et al. (41 and U.S. Pat. No. 5,081,226 to Berzofsky et al.), Hale et al. (42 and U.S. Pat. No. 5,030,449 to Berzofsky et al.) and Palker et al. (55), which are hereby incorporated by reference.

EXAMPLE 11

ADMINISTRATION OF PEPTIDES AS A VACCINE AGAINST HIV

The aim of the research of a large number of biomedical researchers is the production of a vaccine which would produce protection to humans from infection by HIV or therapeutic benefit in AIDS treatment. The instant invention provides peptides that are useful for the preparation of such vaccines as well as specifying six particular peptides as candidates based on the production of a T-cell response to the protein target from which the peptides are derived in mice immunized with the peptide. A pharmaceutical composition including a vaccine in accordance with the present invention comprises an effective antigenic or therapeutic amount of at least one of the peptides and a pharaceutically acceptable carrier such as physiological saline, non-toxic, sterile buffer and the like. A therapeutically effective amount of peptide is an amount in the range of 10 to 1000 μg of peptide per person, preferably about 100 μg. Of course, additives such as preservatives, sterilants, adjuvants and the like, well known to one of ordinary skill in the art, could also be included in the pharmaceutical composition to maintain or increase the efficacy of the preparation.

It is proposed that peptides of the instant invention can also be administered as a vaccine in a fashion similar to that for the administration to primates of a synthetic peptide vaccine against hepatitis B as described by Itoh (60). An alternative method for the preparation of vaccines involves the use of Protein A coated microbeads that bind immune complexes of an antibody and the immunizing antigen on their outer surface described for example in Platt, et al., U.S. Pat. No. 4,493,825, hereby incorporated by reference.

Methods of immunization with peptides to induce $CD8^+$ cytotoxic T cells which could be used include those of Aichele et al (61), Deres et al. (62) and Kast et al. (63).

The invention being thus described, it is clear that the same may be varied in many ways. Such variations are not to be regarded as a departure from the spirit and scope of the invention, and all such modifications as would be obvious to one skilled in the art are intended to be included within the scope of the following claims.

REFERENCES

1. R. N. Germain, Nature, 322:687 (1986): T. J. Braciale et al., Immunol. Rev. 98:95 (1987).
2. A. R. Townsendet al., Cell 44:959 (1986).
3. G. M. Van Bleek and S. G. Nathenson, Nature 348:213 (1990)
4. O. Rotzschke, et al., Nature 348:252 (1990)
5. K. Falk et al., Nature 351:290 (1991)
6. T. Elliott et al., Nature 351:402 (1991)
7. D. R. Madden et al., Nature 353:321 (1991)
8. T. S. Jaredetzky et al., Nature 353:326 (1991)
9. T. N. Schumacher, et al., Nature 350:703 (1991).
10. H. Takahashi, et al., Proc. Natl. Acad. Sci. U.S.A. 85:3105 (1988).
11. H. Takahashi, et al., J. Exp. Med. 170:2023 (1989).
12. M. Clerici, et al., J. Immunol. 146:2214 (1991).
13. S. Kozlowski, et al., Nature 349:74 (1991).
14. K. L. Rock et al., Proc. Natl. Acad. Sci. U.S.A. 87:7517 (1990)
15. A. Vitiello et al., Science 250:1423 (1990)
16. K. L. Rock et al., Proc. Natl. Acad. Sci. U.S.A. 88:301 (1991)
17. K. P. Kane, Eur J. Immunol. 21:2289 (1991).
18. J. D. Ashwell et al., J. Exp. Med. 165:173 (1987).
19. G. M. Hasse and C. A. Ryan, Methods Enzymol. 80:778 (1981).
20. T. H. J. Plummer and T. J. Ryan, Biochem. Biophys. Res. Commun. 98:448 (1981).
21. D. W. Cushman et al., Biochemistry 16:5484 (1977).
22. A. J. Barrett, et al., Biochem. J. 201:189 (1982).
23. K. K. F. Ng and J. R. Vane, Nature 218:144 (1968).
24. J. K. McDonald and A. J. Barret, in *Mammalian Proteases: A Glossary and Bibliography* (Academic Press Inc., London, 1986), vol. 2 Exopeptidases, pp. 227–250 (1986).
25. L. Ratner et al., Nature 313:277 (1985)
26. R. H. Schwartz, Annu. Rev. Immunol. 3:237 (1985)
27. A. S. Rosenthal, Immunol. Rev. 40:136 (1978).
28. B. Benacerraf, J. Immunol. 120:1809 (1978)
29. R. M. Zinkernagel and P. C. Doherty, Adv. Immunol. 27:51 (1979)
30. A. Townsend H. Bodmer, Annu. Rev. Immunol. 7:601 (1989)
31. J. W. Kappler et al., J. Exp. Med. 153:1198 (1981)
32. T. Hfinig and M. J. Bevan, Nature 294:460 (1981)
33. S. M. Hedrick et al., Cell 30:141 (1982)
34. J. Kappler et al., Cell 34:727 (1983)
35. D. L. Perkins et al., J. Exp. Med. 170:279 (1989)
36. J. K. Hickling et al., Internat. Immunol. 2:435 (1990)
37. H. Takahashi et al., Proc. Natl. Acad. Sci. USA 85:3105 (1988).
38. M. Clerici et al., J. Immunol. 146:2214 (1991)
39. H. Takahashi et al., J. Exp. Med. 171:571 (1990)
40. M. Clerici et al., Nature 339:383 (1989)
41. K. B. Cease et al., Proc. Natl. Acad. Sci. USA 84:4249 (1987)
42. P. M. Hale et al., Internat. Immunol. 1:409 (1989)
43. J. A. Berzofsky et al., Nature 334:706 (1988)
44. F. Sinigaglia et al., Nature 336:778 (1988)
45. P. Panina-Bordignon et al., Eur. J. Immunol. 19:2237 (1989)
46. J. A. Berzofsky, J. Acq. Immune Defic. Syndromes 4:451 (1991)
47. S. Chakrabarti et al., Nature 320:535 (1986)
48. R. A. Houghten, Proc. Natl. Acad. Sci. USA. 82:5131 (1985)
49. A. R. Townsend et al., Cell 44:959 (1986)
50. H. Takahashi et al., J. Exp. Med. 170:2023 (1989)
51. A. Kurata et al., J. Immunol. 143:2024 (1989)
52. S. J. Brett et al., J. Immunol. 143:771 (1989)
53. C. M. Walker et al., Science 234:1563 (1986)
54. H. Tsubota et al., J. Exp. Med. 169:1421 (1989)
55. T. J. Palker et al., J. of Immunology 142:3612 (1989)
56. K. Kitamura et al., Biochem. Biophys. Res. Comm. 169:1164 (1990)
57. C. J. Dickson and T. Yamada, J. Biol. Chem. 266:334 (1991)
58. K. Suzuki et al., EMBO J. 9:4259 (1990)
59. G. A. Katopodis et al., *Biochemistry* 30:6189 (1991)
60. Y. Itoh et al., *Proc. Natl. Acad. Sci. USA* 83:9174 (1986)
61. P. Aichele et al., J. Exp Med. 171:1815 (1990)
62. K. Deres et al., Nature 342:561 (1989)
63. W. K. Kast et al., Proc. Natl. Acad. Sci. USA 88:2283 (1991)
64. H. Takahashi et al., Science 246:118 (1989)

What is claimed is:

1. An isolated polypeptide consisting of the amino acid sequence RGPGRAFVTI (residues 4–13 of SEQ ID NO. 1), wherein said polypeptide stimulates cytotoxic T lymphocytes.

2. An isolated polypeptide consisting of the amino acid sequence IGPGRAFYTT (residues 4–13 of SEQ ID NO. 2), wherein said polypeptide stimulates cytotoxic T lymphocytes.

3. An isolated polypeptide consisting of an amino acid sequence selected from the group consisting of RIHIGPGRFYTTKN (SEQ ID NO:2), SITKGPGRVIYATGQ (SEQ ID NO:3), SIHIGPGRAFYATGD (SEQ ID NO:4), SLSIGPGRAFRTREI (SEQ ID NO:5), SISIGPGRAFFATTD (SEQ ID NO:6), SIYIGPGRAFHTTGR (SEQ ID NO:7), GIAIGPGRTLYAREK (SEQ ID NO:8), RVTLGPGRVWYTTGE (SEQ ID NO:9), SIRIGPGKVFTAKGG (SEQ ID NO:10), GIHFGPGQALYTTGI (SEQ ID NO:11), STPIGLGQALYTTRG (SEQ ID NO:12), STPIGLGQALYTTRI (SEQ ID NO:13), and RTPTGLGQSLYTTRS (SEQ ID NO:14).

4. An isolated polypeptide consisting of an amino acid sequence selected from the group consisting of IGPGRAFYAT (residues 4–13 of SEQ ID NO:4), KGPGRVIYAT (residues 4–13 of SEQ ID NO:3), IGPGRAFHTT (residues 4–13 of SEQ ID NO:7), IGPGRTLYAFR (residues 4–13 of SEQ ID NO:8), LGPGRVWYTT (residues 4–13 of SEQ ID NO:9), IGPGRAFRTR (residues 4–13 of SEQ ID NO:5), GPGRAFVTI (residues 5–13 of SEQ ID NO:1), RGPGRAFVT (residues 5–12 of SEQ ID NO:1), QRGPGRAFV (residues 3–11 of SEQ ID NO:1), and IQRGPGRAFV (residues 2–11 of SEQ ID NO:1).

5. An isolated polypeptide consisting of an amino acid sequence DRVIEVVQGATRAIR (SEQ ID NO:16).

* * * * *